(12) United States Patent
Bridge et al.

(10) Patent No.: US 11,416,872 B2
(45) Date of Patent: Aug. 16, 2022

(54) SYSTEMS AND METHODS FOR TRACKING GREENHOUSE GAS EMISSIONS ASSOCIATED WITH AN ENTITY

(71) Applicant: DYNACERT INC., Toronto (CA)

(72) Inventors: David Bridge, Mississauga (CA); Ruston Jeroen Hoffman, Grimsby (CA)

(73) Assignee: DYNACERT INC., Toronto (CA)

( * ) Notice: Subject to any disclaimer, the term of this patent is extended or adjusted under 35 U.S.C. 154(b) by 103 days.

(21) Appl. No.: 16/875,843

(22) Filed: May 15, 2020

(65) Prior Publication Data
US 2020/0278333 A1 Sep. 3, 2020

Related U.S. Application Data

(63) Continuation of application No. 16/837,032, filed on Apr. 1, 2020, now Pat. No. 11,270,319, which is a
(Continued)

(51) Int. Cl.
*G06Q 30/00* (2012.01)
*G01N 33/00* (2006.01)
(Continued)

(52) U.S. Cl.
CPC ....... *G06Q 30/018* (2013.01); *G01N 33/0062* (2013.01); *G01N 33/0075* (2013.01);
(Continued)

(58) Field of Classification Search
CPC ...... G06Q 30/018; G06Q 10/10; G06Q 40/04; G06Q 50/26; G01N 33/0062; G01N 33/0075
(Continued)

(56) References Cited

U.S. PATENT DOCUMENTS 6,904,336 B2   6/2005   Raines et al.
7,343,341 B2   3/2008   Sandor et al.
(Continued)

OTHER PUBLICATIONS

Fu et al., "Blockchain Enhanced Emission Trading Framework in Fashion Apparel Manufacturing Industry", Sustainability, MDPI, Mar. 19, 2018.*
(Continued)

*Primary Examiner* — Frantzy Poinvil
(74) *Attorney, Agent, or Firm* — Bereskin & Parr LLP/S.E.N.C.R.L., s.r.l.

(57) ABSTRACT

Various embodiments are described herein for methods, devices and systems that can be used to track at least one emission type generated, directly or indirectly, by an entity. In one example embodiment, the system includes an emission tracking device coupled to the entity, where the emission tracking device receives a first emission data received at a first time and a second emission data received at a second time after implementation of one or more emission reduction steps. The system further includes an external processor in communication with the emission tracking device, where the external processor is configured to analyze the first emission data to determine an emission baseline, analyze the second emission data to determine a second emission output value, and determine an emission offset measurement corresponding to the at least one emission type based on the emission baseline and the second emission output value.

30 Claims, 8 Drawing Sheets

Related U.S. Application Data continuation of application No. PCT/CA2018/051235, filed on Oct. 2, 2018.

(60) Provisional application No. 62/567,392, filed on Oct. 3, 2017.

(51) Int. Cl.
  *G06Q 10/10* (2012.01)
  *G06Q 40/04* (2012.01)
  *G06Q 50/26* (2012.01)

(52) U.S. Cl.
  CPC ............ *G06Q 10/10* (2013.01); *G06Q 40/04* (2013.01); *G06Q 50/26* (2013.01); *G01N 2033/0068* (2013.01)

(58) Field of Classification Search
  USPC ....................................................... 705/3–44
  See application file for complete search history.

(56) References Cited

U.S. PATENT DOCUMENTS

| | | | |
|---|---|---|---|
| 7,877,235 B2 * | 1/2011 | McConnell ............ | G06Q 10/06 702/188 |
| 7,930,144 B2 | 4/2011 | McConnell et al. | |
| 7,957,981 B2 * | 6/2011 | Zimmerman .......... | G06Q 10/04 705/1.1 |
| 7,983,929 B2 | 7/2011 | Zimmerman | |
| 8,655,791 B2 | 2/2014 | Zimmerman | |
| 9,152,994 B2 | 10/2015 | Marino | |
| 2004/0158478 A1 | 8/2004 | Zimmerman | |
| 2005/0137900 A1 * | 6/2005 | Werner ............ | G06Q 10/06375 705/37 |
| 2007/0192221 A1 | 8/2007 | Sandor et al. | |
| 2007/0260405 A1 | 11/2007 | McConnell et al. | |
| 2008/0015976 A1 * | 1/2008 | Sandor ................... | G06Q 40/04 705/37 |
| 2008/0154671 A1 | 6/2008 | Delk | |
| 2008/0167772 A1 | 7/2008 | Du et al. | |
| 2008/0177563 A1 | 7/2008 | Zimmerman | |
| 2008/0183523 A1 | 7/2008 | Dikeman | |
| 2008/0255899 A1 | 10/2008 | McConnell et al. | |
| 2008/0275815 A1 * | 11/2008 | Musier ................... | G06Q 20/10 705/39 |
| 2009/0043687 A1 * | 2/2009 | van Soestbergen ... | G06Q 40/00 705/37 |
| 2009/0132176 A1 | 5/2009 | McConnell et al. | |
| 2009/0171975 A1 | 7/2009 | McConnell et al. | |
| 2009/0271258 A1 * | 10/2009 | Quinn ................ | G06Q 30/0207 705/14.1 |
| 2009/0287520 A1 | 11/2009 | Zimmerman | |
| 2011/0087508 A1 * | 4/2011 | McConnell ...... | G06Q 10/06375 705/7.11 |
| 2013/0218446 A1 | 8/2013 | Bradley et al. | |
| 2013/0246133 A1 * | 9/2013 | Dembo ................ | G06Q 30/018 705/14.1 |
| 2014/0089078 A1 * | 3/2014 | Dessert .............. | G06Q 30/0238 705/14.38 |
| 2014/0315528 A1 | 10/2014 | Gupta | |
| 2016/0055596 A1 | 2/2016 | Dilip et al. | |
| 2020/0148072 A1 * | 5/2020 | Ashley ................... | G06Q 50/06 |

OTHER PUBLICATIONS

Extended European Search Report issued in EP Patent Application No. 18864809.1 dated Mar. 9, 2021 (8 pages).

Non-Final Office Action and Notice of References dated Aug. 2, 2021 in U.S. Appl. No. 16/837,032 (11 pages).

International Search Report and Written Opinion dated Jan. 7, 2019 in corresponding PCT Patent Application No. PCT/CA2018/051235 (8 pages).

Notice of Allowance and Fee(s) Due and Notice of References dated Nov. 23, 2021 in U.S. Appl. No. 16/837,032 (14 pages).

Xu Nan et al. An Overview of Eco-Driving Theory, Capability Evaluation and Training Applications. Sensors, vol. 21.19: 6547, published Sep. 30, 2021, (24 pages).

Motsinger et al. A Gold Standard for Equity in Climate Cap-and-Trade Programs. Environment, vol. 52(4), published Jun. 29, 2010, pp. 34-43.

* cited by examiner

SYSTEMS AND METHODS FOR TRACKING GREENHOUSE GAS EMISSIONS ASSOCIATED WITH AN ENTITY

CROSS-REFERENCE TO RELATED APPLICATION

This application is a continuation of U.S. patent application Ser. No. 16/837,032, now, U.S. Pat. No. 11,270,319 filed Apr. 1, 2020, which is a continuation of International Patent Application No. PCT/CA2018/051235, filed Oct. 2, 2018, which claims priority from the U.S. Provisional Patent Application No. 62/567,392, filed on Oct. 3, 2017; the entire contents of each of which are hereby incorporated by reference.

FIELD

The described embodiments relate to systems and methods for tracking emissions associated with an entity, and in particular, to systems and methods for tracking greenhouse gas emissions associated with an entity.

BACKGROUND

Conventional systems for analyzing and reporting greenhouse gas emissions from a facility typically rely on receiving emission related information from users, for example via surveys. Consequently, the conventional systems are typically inaccurate and inefficient. There is a need to improve as well as to expand the applicability of such systems.

SUMMARY

In one aspect, in at least one embodiment described herein, there is provided a system for tracking at least one emission type generated by an entity, where the entity generating one or more emissions types including the at least one emission type. The system comprises at least one emission tracking device communicably coupled to the entity, the at least one emission tracking device being configured to receive emission data associated with the at least one emission type, the emission data including a first emission data received at a first time and a second emission data received at a second time, wherein the second emission data is received after implementation of at least one emission reduction step corresponding to the at least one emission type; and an external processor in communication with the at least one emission tracking device, the external processor being configured to: analyze the first emission data received at the first time to determine a first emission output value designated as an emission baseline; analyze the second emission data received at the second time to determine a second emission output value; and determine an emission offset measurement corresponding to the at least one emission type based on the emission baseline and the second emission output value.

In some embodiments, the at least one emission tracking device is configured to interface with one or more emission sensors located within the entity, the one or more emission sensors being configured to measure the at least one emission type.

In some other embodiments, the at least one emission tracking device is configured to interface with one or more emission monitoring devices located within the entity, the one or more emission monitoring devices being configured to measure the at least one emission type.

In some other embodiments, the at least one emission tracking device is configured to interface with one or more secondary emission sources to receive secondary data corresponding to the at least one emission type.

In some embodiments, the one or more secondary emission sources are located within the entity.

In some embodiments, the external processor is configured to compare the emission baseline to an emission standard for the at least one emission type, and wherein the at least one emission reduction step is based on the comparison.

In some embodiments, the external processor is configured to generate at least one emission report associated with the emission offset measurement.

In some embodiments, the external processor is configured to determine carbon credits available for trading based on the emission offset measurement.

In some embodiments, the at least one emission tracking device is configured to determine if the at least one emission type is being monitored within the entity by one or more emission sensors, and interface with the one or more emission sensors if the entity is determined to be monitored.

In some embodiments, the at least one emission tracking device is configured to determine a number of emission sensors required by the entity if the entity is determined not to be monitored.

In some embodiments, the at least one emission tracking device is configured to verify accuracy of the one or more emission sensors if the entity is determined to be monitored.

In some embodiments, the at least one emission type is selected from the group consisting of carbon monoxide, carbon dioxide, methane, ozone, chlorofluorocarbons, sulfur oxides, nitrogen oxides, non-methane volatile organic compounds, ammonia, and peroxyacetyl nitrate.

In some embodiments, the entity is selected from the group consisting of an agricultural facility, an industrial facility, a commercial facility, a power generation facility, a commercial building, a medical building, an educational building, a residential building, a single-family residence, a household, a rail transportation means, an air transportation means, a marine transportation means, an on-road transportation means, and an off-road transportation means.

In another aspect, in at least one embodiments described herein, there is provided a system for tracking at least one emission type generated by an entity, where the entity generating one or more emissions types including the at least one emission type. The system comprises: a communication network; a non-transient computer memory; and at least one processor coupled to the non-transient computer memory and the communication network, the at least one processor being configured to: receive emission data associated with the at least one emission type, the emission data including a first emission data received at a first time and a second emission data received at a second time, wherein the second emission data is received after implementation of at least one emission reduction step corresponding to the at least one emission type; analyze the first emission data received at the first time to determine a first emission output value designated as an emission baseline; analyze the second emission data received at the second time to determine a second emission output value; and determine an emission offset measurement corresponding to the at least one emission type based on the emission baseline and the second emission output value.

In some embodiments, the at least one processor is configured to interface with one or more emission sensors located within the entity, the one or more emission sensors being configured to measure the at least one emission type.

In some embodiments, the at least one processor is configured to interface with one or more emission monitoring devices located within the entity, the one or more emission monitoring devices being configured to measure the at least one emission type.

In some embodiments, the at least one processor is configured to interface with one or more secondary emission sources to receive secondary data corresponding to the at least one emission type.

In some embodiments, the one or more secondary emission sources are located within the entity.

In some embodiments, the at least one processor is configured to compare the emission baseline to an emission standard for the at least one emission type, and wherein the at least one emission reduction step is based on the comparison.

In some embodiments, the at least one processor is configured to generate at least one emission report associated with the emission offset measurement.

In some embodiments, the at least one processor is configured to determine carbon credits available for trading based on the emission offset measurement.

In some embodiments, the at least one processor is configured to determine if the at least one emission type is being monitored within the entity by one or more emission sensors, and interface with the one or more emission sensors if the entity is determined to be monitored.

In some embodiments, the at least one processor is configured to determine a number of emission sensors required by the entity if the entity is determined not to be monitored.

In some embodiments, the at least one processor is configured to verify accuracy of the one or more emission sensors if the entity is determined to be monitored.

In some embodiments, the at least one emission type is selected from the group consisting of carbon monoxide, carbon dioxide, methane, ozone, chlorofluorocarbons, sulfur oxides, nitrogen oxides, non-methane volatile organic compounds, ammonia, and peroxyacetyl nitrate.

In some embodiments, the entity is selected from the group consisting of an agricultural facility, an industrial facility, a commercial facility, a power generation facility, a commercial building, a medical building, an educational building, a residential building, a single-family residence, a household, a rail transportation means, an air transportation means, a marine transportation means, an on-road transportation means, and an off-road transportation means.

In another aspect, in at least one embodiment described herein, there is provided a method for tracking at least one emission type generated by an entity, where the entity generating one or more emissions types including the at least one emission type. The method comprises: receiving a first emission data associated with the at least one emission type at a first time; analyzing the first emission data received at the first time to determine a first emission output value designated as an emission baseline; recommending at least one emission reduction step corresponding to the at least one emission type; receiving a second emission data associated with the at least one emission type at a second time, wherein the second emission data is received after implementation of the at least one emission reduction step; analyzing the second emission data received at the second time to determine a second emission output value; and determining an emission offset measurement corresponding to the at least one emission type based on the emission baseline and the second emission output value.

In some embodiments, the method further comprises interfacing with one or more emission sensors located within the entity to receive the first emission data and the second emission data, the one or more emission sensors being configured to measure the at least one emission type.

In some embodiments, the method further comprises interfacing with one or more emission monitoring devices located within the entity to receive the first emission data and the second emission data, the one or more emission monitoring devices being configured to measure the at least one emission type.

In some embodiments, the method further comprises interfacing with one or more secondary emission sources to receive a first secondary data corresponding to the at least one emission type at the first time and a second secondary data corresponding to the at least one emission type at the second type, wherein the first emission data is based on the first secondary data and the second emission data is based on the second secondary data.

In some embodiments, the one or more secondary emission sources are located within the entity.

In some embodiments, the method further comprises comparing the emission baseline to an emission standard for the at least one emission type, and determining the at least one emission reduction step based on the comparison.

In some embodiments, the method further comprises generating at least one emission report associated with the emission offset measurement.

In some embodiments, the method further comprises determining carbon credits available for trading based on the emission offset measurement.

In some embodiments, the at least one emission type is selected from the group consisting of carbon monoxide, carbon dioxide, methane, ozone, chlorofluorocarbons, sulfur oxides, nitrogen oxides, non-methane volatile organic compounds, ammonia, and peroxyacetyl nitrate.

In some embodiments, the entity is selected from the group consisting of an agricultural facility, an industrial facility, a commercial facility, a power generation facility, a commercial building, a medical building, an educational building, a residential building, a single-family residence, a household, a rail transportation means, an air transportation means, a marine transportation means, an on-road transportation means, and an off-road transportation means.

In another aspect, in at least one embodiment described herein, there is provided a system for tracking at least one emission type generated by an entity, where the entity generating one or more emissions types including the at least one emission type. The system comprises: a communication network; a non-transient computer memory; and at least one processor coupled to the non-transient computer memory and the communication network, the at least one processor being configured to: receive a first emission data associated with the at least one emission type at a first time; analyze the first emission data received at the first time to determine a first emission output value designated as an emission baseline; recommend at least one emission reduction step corresponding to the at least one emission type; receive a second emission data associated with the at least one emission type at a second time, wherein the second emission data is received after implementation of the at least one emission reduction step; analyze the second emission data received at the second time to determine a second emission output value; and determine an emission offset measurement corresponding to the at least one emission type based on the emission baseline and the second emission output value.

In another embodiment, the at least one processor is configured to perform the methods as defined above or other methods in accordance with the teachings herein.

In another aspect, in at least one embodiment described herein, there is provided a computer-readable medium storing computer-executable instructions, the instructions for causing a processor to perform a method of tracking at least one emission type generated by an entity, the entity generating one or more emissions types including the at least one emission type, the method comprising: receiving a first emission data associated with the at least one emission type at a first time; analyzing the first emission data received at the first time to determine a first emission output value designated as an emission baseline; recommending at least one emission reduction step corresponding to the at least one emission type; receiving a second emission data associated with the at least one emission type at a second time, wherein the second emission data is received after implementation of the at least one emission reduction step; analyzing the second emission data received at the second time to determine a second emission output value; and determining an emission offset measurement corresponding to the at least one emission type based on the emission baseline and the second emission output value.

In some embodiments, the instructions cause the processor to perform the methods as described above or other methods in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from the detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment and the figures will now be briefly described.

Figure 1:
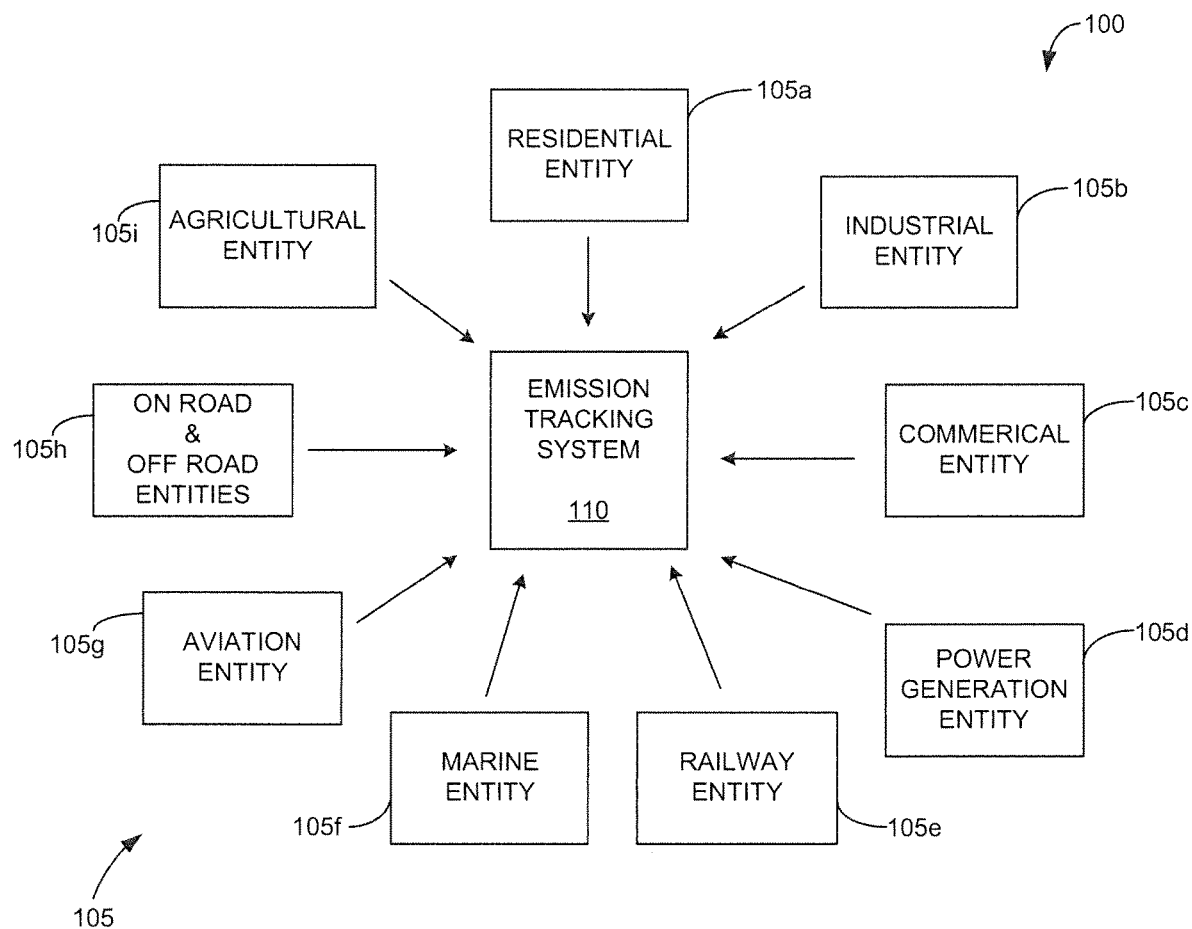
FIG. 1 is an example of a block diagram of an emission tracking platform.

The skilled person in the art will understand that the drawings, described below, are for illustration purposes only. The drawings are not intended to limit the scope of the applicants' teachings in anyway. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

Various apparatuses or processes will be described below to provide an example of at least one embodiment of the claimed subject matter. No embodiment described below limits any claimed subject matter and any claimed subject matter may cover processes, apparatuses, devices or systems that differ from those described below. The claimed subject matter is not limited to apparatuses, devices, systems or processes having all of the features of any one apparatus, device, system or process described below or to features common to multiple or all of the apparatuses, devices, systems or processes described below. It is possible that an apparatus, device, system or process described below is not an embodiment of any claimed subject matter. Any subject matter that is disclosed in an apparatus, device, system or process described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It should also be noted that the terms "coupled" or "coupling" as used herein can have several different meanings depending in the context in which the term is used. For example, the term coupling can have a mechanical or electrical connotation. For example, as used herein, the terms "coupled" or "coupling" can indicate that two elements or devices can be directly connected to one another or connected to one another through one or more intermediate elements or devices via an electrical element, electrical signal or a mechanical element such as but not limited to, a wire or a cable, for example, depending on the particular context.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

The various embodiments of the devices, systems and methods described herein may be implemented using a combination of hardware and software. These embodiments may be implemented in part using computer programs executing on programmable devices, each programmable device including at least one processor, an operating system, one or more data stores (including volatile memory or non-volatile memory or other data storage elements or a combination thereof), at least one communication interface and any other associated hardware and software that is necessary to implement the functionality of at least one of the embodiments described herein. For example, and without limitation, the computing device may be a server, a network appliance, an embedded device, a computer expansion module, a personal computer, a laptop, a personal data assistant, a cellular telephone, a smart-phone device, a tablet computer, a wireless device or any other computing device capable of being configured to carry out the methods described herein. The particular embodiment depends on the application of the computing device.

In some embodiments, the communication interface may be a network communication interface, a USB connection or another suitable connection as is known by those skilled in the art. In other embodiments, the communication interface may be a software communication interface, such as those for inter-process communication (IPC). In still other embodiments, there may be a combination of communication interfaces implemented as hardware, software, and a combination thereof.

In at least some of the embodiments described herein, program code may be applied to input data to perform at least some of the functions described herein and to generate output information. The output information may be applied to one or more output devices, for display or for further processing.

At least some of the embodiments described herein that use programs may be implemented in a high level procedural or object oriented programming and/or scripting language, or both. Accordingly, the program code may be written in C, Java, SQL or any other suitable programming language and may comprise modules or classes, as is known to those skilled in object oriented programming. However, other programs may be implemented in assembly, machine language or firmware as needed. In either case, the language may be a compiled or interpreted language.

The computer programs may be stored on a storage media (e.g. a computer readable medium such as, but not limited to, ROM, magnetic disk, optical disc) or a device that is readable by a general or special purpose computing device. The program code, when read by the computing device, configures the computing device to operate in a new, specific and predefined manner in order to perform at least one of the methods described herein.

Furthermore, some of the programs associated with the system, processes and methods of the embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The various embodiments disclosed herein generally relate to systems and methods of tracking emissions associated with an entity. In particular, the systems and methods relate to tracking greenhouse gas emissions associated with an entity. Some non-limiting examples of greenhouse gas emissions may include one or more of carbon monoxide, carbon dioxide, methane, ozone, chlorofluorocarbons, sulfur oxides, nitrogen oxides, non-methane volatile organic compounds, ammonia, and peroxyacetyl nitrate, among others.

Reference is first made to FIG. 1, illustrating an emission tracking platform 100 according to an example embodiment. The emission tracking platform 100 comprises an emission tracking system 110 and one or more entities 105.

An entity can be defined as any greenhouse gas emitting establishment or asset. Some non-limiting examples of an entity include a residential building 105a (e.g. a single-family residence, a townhouse, a condominium, an apartment building, etc.), an industrial facility 105b (e.g. a factory), a commercial facility 105c (e.g. a medical building, an educational building etc.), a power generation facility 105d, a rail transportation means 105e, a marine transportation means 105f, an air transportation means 105g, an on-road and off-road transportation means 105h, and an agricultural facility 105i.

The emission tracking system 110 comprises one or more devices communicably coupled to each other and to the one or more entities 105. In the various embodiments illustrated herein, the emission tracking system 110 is configured to track one or more greenhouse gas emissions associated with one or more entities 105.

In the various embodiments illustrated herein, greenhouse gas emissions are considered to be generated or associated with an entity 105 if the operation of the entity results in direct or indirect generation of greenhouse gas emissions. For example, for an entity such as an industrial facility 105b, the greenhouse gas emissions associated with the entity 105b will include any greenhouse gas released by the entity 105b itself during its operation as well as any greenhouse gas released by any other entity, such as a power generation facility 105d, due to the power consumption by the entity 105b.

In the various embodiments illustrated herein, tracking may include a variety of steps as discussed here. Some non-limiting examples of tracking including steps such as monitoring, measuring, analyzing and reporting greenhouse gas emission related information associated with an entity 105.

In one example, the emission tracking system 110 includes a first device configured to monitor and/or measure greenhouse gas emissions from an entity 105; log and compile gathered data to generate real time emission measurements; determine total emission output from the entity 105; and transfer the gathered data, measurements and calculations to a second device.

In this example, the second device is configured to receive data, measurements and calculations from the first device; conduct analysis on the received information; determine changes in emissions output to validate compliance; determine amount of greenhouse gas credit or offset (e.g. carbon credit etc.) required or available for trade; facilitate or broker a trade in greenhouse gas emission credit; monitor emission reduction efforts and techniques; and generate and transmit corresponding reports.

In another example, the emission tracking system 110 includes a single device capable of performing the functionalities of both the first device and the second device of the previous example. Emission tracking system 110 is explained in further detail below, particularly in relation to FIGS. 3-7.

Figure 2A:
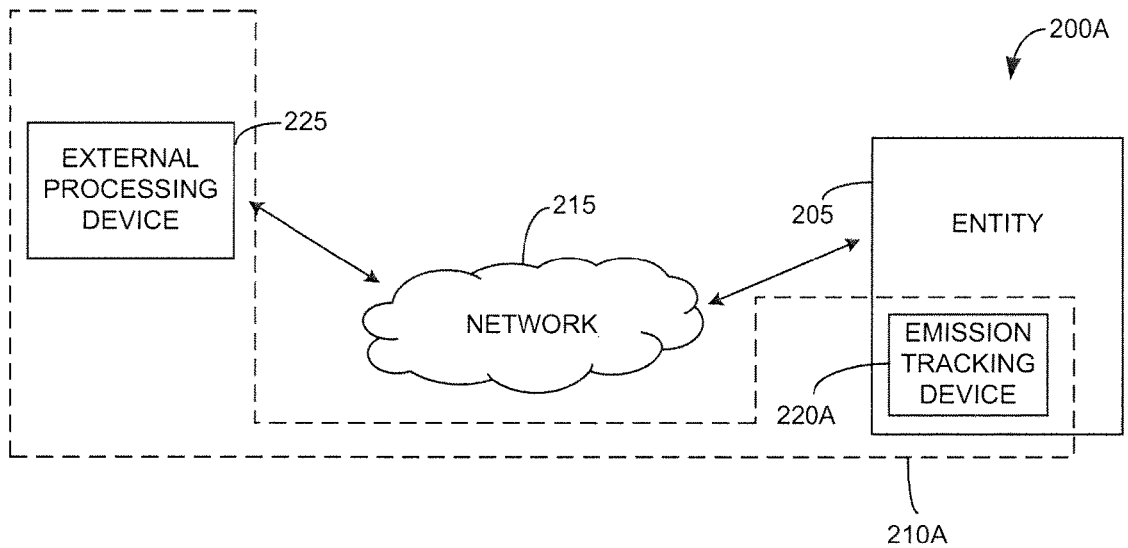
FIG. 2A is another example of a block diagram of an emission tracking platform.
Figure 2B:
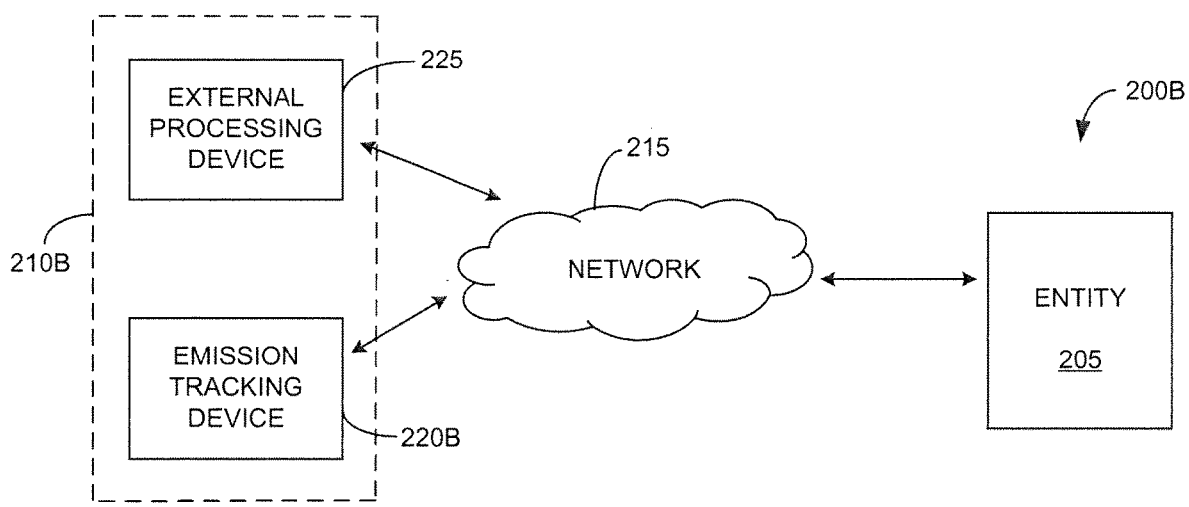
FIG. 2B is a further example of a block diagram of an emission tracking platform.
Figure 2C:
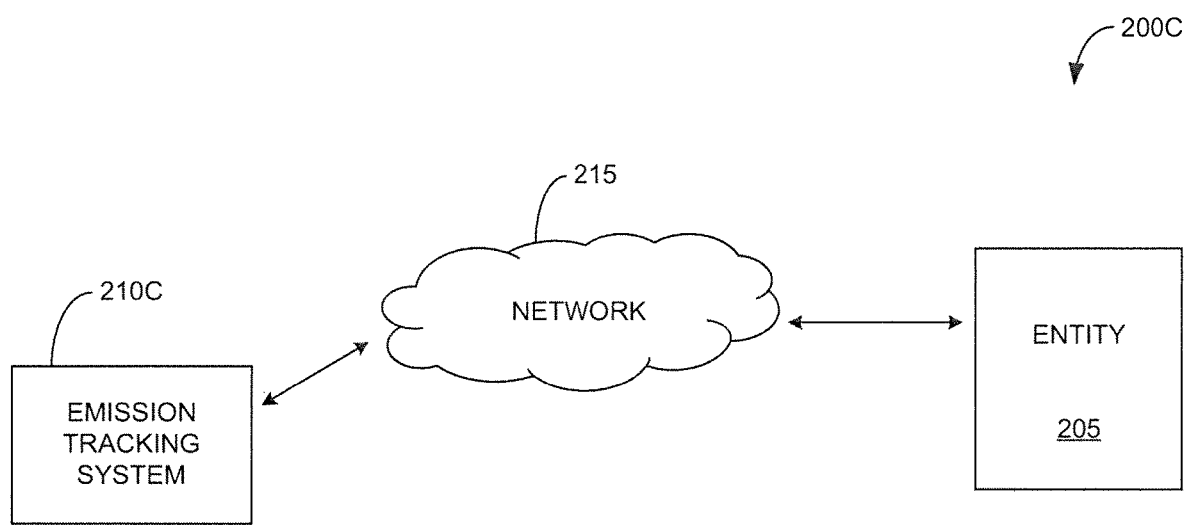
FIG. 2C is another example of a block diagram of an emission tracking platform.

Reference is briefly made to FIGS. 2A-2C, illustrating different examples of emission tracking platforms. FIG. 2A illustrates an emission tracking platform 200A according to one example. FIG. 2B illustrates an emission tracking platform 200B according to another example. FIG. 2C illustrates an emission tracking platform 200C according to a further example.

As illustrated in FIG. 2A, emission tracking platform 200A comprises an entity 205, a network 215, and an emission tracking system 210A. In this embodiment, the emission tracking system 210 comprises an emission tracking device 220A and an external processing device 225.

Network 215 may be any network(s) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these. Network 215 may also include a storage medium, such as, for example, a CD ROM, a DVD, an SD card, an external hard drive, a USB drive, etc.

In the illustrated embodiment, the emission tracking system 220A is located within the premises of entity 205, and the external processing device is located separate from the emission tracking device 220A. The emission tracking device 220A is communicably coupled to the external processing device 225 via the network 215.

In the embodiment illustrated in FIG. 2B, emission tracking platform 200B comprises an entity 205, a network 215, and an emission tracking system 210B. In this embodiment, the emission tracking system 210B comprises an emission tracking device 220B and an external processing device 225.

In the illustrated embodiment, the emission tracking system 220B is not in the same physical location as the premises of entity 205, and is communicably coupled to the entity 205 via network 215. In addition, the emission tracking device 220B is communicably coupled to the external processing device 225 via network 215.

In the embodiment illustrated in FIG. 2C, emission tracking platform 200C comprises an entity 205, a network 215, and an emission tracking system 210C. In this embodiment, the functionalities of an emission tracking device, such as the emission tracking devices 220A, 220B of FIGS. 2A and 2B, and an external processing device, such as the external processing device 225 of FIGS. 2A and 2B, are combined into one hardware unit indicated as emission tracking system 210C in FIG. 2C.

The emission tracking system 210C may or may not be located in the same physical location as the premises of entity 205. The emission tracking system 210C is communicably coupled to the entity 205 via network 215.

In the various embodiments of FIGS. 2A-2C, the emission tracking systems 210A, 210B and 210C are configured to track greenhouse gas emissions, corresponding to one or more greenhouse gases, associated with the entity 205. As discussed above, tracking may include one or more non-limiting steps of monitoring, measuring, analyzing and reporting the greenhouse gas emissions associated with the entity 205.

In embodiments where the emission tracking devices, such as devices 220A, 220B of FIGS. 2A, 2B are separate from the external processing devices, such as external processing devices 225 of FIGS. 2A, 2B, the emission tracking devices 220A, 220B may be configured to carry out one or more non-limiting steps of monitoring, measuring, analyzing and reporting emission data, and the external processing device 225 may be configured to carry out the other non-limiting steps of monitoring, measuring, analyzing and reporting emission data.

For example, in one case, the emission tracking devices 220A, 220B may be configured to carry out the monitoring and measuring steps, and the external processing device 225 may be configured to carry out the analyzing and reporting steps. In another case, the emission tracking devices 220A, 220B may be configured to carry out the monitoring step, and the external processing device 225 may be configured to carry out the measuring, analyzing and reporting steps. In a further case, the emission tracking devices 220A, 220B may be configured to carry out the monitoring, measuring and analyzing steps, and the external processing device 225 may be configured to carry out the reporting step.

Figure 3:
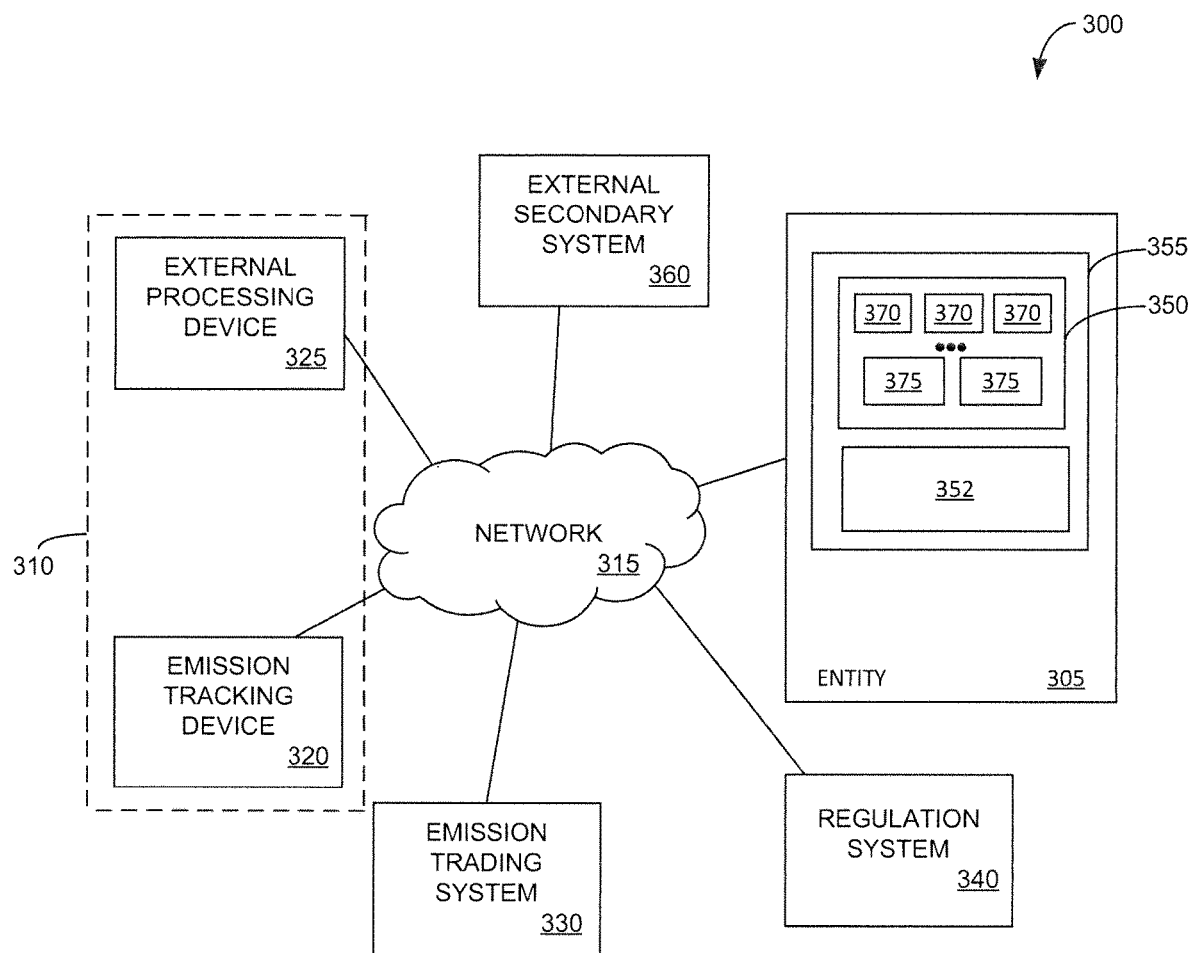
FIG. 3 is an example of a block diagram of an emission tracking platform.

Reference is next made to FIG. 3, illustrating an emission tracking platform 300 according to an example embodiment. Emission tracking platform 300 comprises an entity 305, a network 315 and an emission tracking system 310. Emission tracking platform further comprises an emission trading system 330, a regulation system 340 and an external secondary system 360.

In the illustrated embodiment, entity 305 comprises an emission monitoring system 355. The emission monitoring system 355 includes a plurality of primary 350 and internal secondary 352 sources for monitoring and/or otherwise providing information related to greenhouse gas emissions associated with the entity 305.

Primary sources 350 are defined as one or more units, devices and/or systems that are capable of directly monitoring the greenhouse gas emissions from the entity 305. Primary sources 350 may include one or more sensors 370 (e.g. carbon monoxide sensor, carbon dioxide sensor, etc.), emission monitoring devices 375 (e.g. continuous emissions monitoring system or CEM, portable emission monitoring system or PEM, etc.), and/or any other system or equipment capable of directly monitoring one or more types of greenhouse gas emissions from the entity 305.

An entity 305 may have one or more sensors 370 configured to directly measure one or more types of greenhouse gas emissions. For example, an entity 305 may have one or more sensors capable of monitoring greenhouse gas emissions such as nitrogen oxides ($NO_x$), carbon dioxide ($CO_2$), oxygen ($O_2$), methane ($CH_4$), carbon monoxide (CO) and non-methane volatile organic compounds (CH), among other gases.

In the illustrated embodiment, the emission tracking system 310 is configured to communicate with sensors 370 via network 315 and receive one or more detected greenhouse gas emission information from the sensors 370. In some cases, the emission tracking system 310 comprises an emission tracking device 320 and a separately located external processing device 325, and in such embodiments, the emission tracking device 320 communicably connects with the sensors 370 and receives detected greenhouse gas emission information.

In some cases, the emission tracking device 320 is located within the premises of the entity 305. In some other cases, emission tracking device 320 is located external to the entity 305. The emission tracking device 320 may be connected to the sensors 370 either via a wired connection or a wireless connection.

The emission tracking system 310 may interface with a sensor 370 via an output connection from the sensor 370. For example, the emission tracking system 310 interfaces with the serial output port of the sensor 370. In some cases, such as in cases where no auxiliary output from the sensor 370 is available, the emission tracking system 310 may interface with the sensor 370 via the circuit board of the sensor 370. For example, the emission tracking system 310 is directly wired (e.g. via a direct splice) to the circuit board of the sensor 370.

The emission tracking system 310 may be configured to receive monitored emission data in the form of electrical signals from the sensors 370. The mission tracking system 310 then processes the received signals to convert them into a value or a measurement indicative of emission output from the entity 305. The emission tracking system 310 is additionally configured to compile, log and analyze the determined emission values or outputs.

The emission tracking system 310 may be configured to validate the sensors 370 to ensure that the received signals are accurate. The emission tracking system 310 can accomplish this by checking the sensors 370 for certification. If the sensors 370 are found to be certified by a regulatory body, no further validation may be required. On the other hand, if the emission tracking system 310 determines that the sensors 370 are not certified, the emission tracking system 310 may validate the sensors 370, for example, by carrying out a calibration check.

As illustrated, primary sources 350 in the monitoring system 355 may also include emission monitoring devices 375. Emission monitoring devices 375 may be any systems or devices capable of measuring greenhouse gas emissions from the entity 305. Emission monitoring devices 375 differ from sensors 370 in that the emission monitoring devices 375 are more complex systems than sensors 370 and are typically configured to monitor more than one greenhouse gas emissions from the entity 305. On the other hand, each sensor 370 monitors a unique type of greenhouse gas emission from the entity 305.

The emission monitoring devices 375 may be certified or non-certified systems. The emission monitoring devices 375 may be a third party or original equipment manufacturer (OEM) measuring equipment. As mentioned above, emission monitoring devices 375 may include a certified continuous emissions monitoring system (CEM system), a certified portable emissions monitoring system (PEM system), among other devices.

A CEM system can be defined as a system comprising equipment and programs configured to analyze one or several specific compounds in the gaseous effluent emissions of a discharge unit or an entity 305. A CEM system may quantify the amount of specific compounds emitted per unit time, and process the information for reporting the emissions. The emissions can be reported in any manner, including, for example, in a manner required by the entity 305. In another example, the emissions can be reported in a manner prescribed by a regulation authority, such as a government body. In one example, the emissions are reported in a manner prescribed by the Environmental Protection Act, Ontario Regulation 194/05 (O. Reg. 194/05). A PEM system can be defined as any system able to predict the concentration and emission rate of a contaminant based on correlation(s) with other monitored parameters.

In the illustrated embodiment, the emission tracking system 310 is configured to interface with the emission monitoring devices 375 via network 315 and receive greenhouse gas emission data corresponding to one or more types of greenhouse gas emissions generated by the entity 305. The emission tracking system 310 may be coupled to emission monitoring devices 375 via wired or wireless connections.

The emission tracking system 310 may receive emission data for each monitored greenhouse gas emission in the form of electrical signals from the emission monitoring devices 375. In such cases, the emission tracking system 310 may process the received signals for each type of monitored greenhouse gas and generate a value or a measurement indicative of total emission output for that greenhouse gas generated by the entity 305. The value or measurement may be determined based on hysteresis or statistical analysis of the monitored emission data.

In some cases, the emission monitoring devices 375 may themselves calculate a total emission output for each type of monitored greenhouse gas from the entity 305, and transmit the total emission output data to the emission tracking system 310. In such cases, the emission tracking system 310 logs, compiles and analyzes the received total emission output data for each monitored greenhouse gas for compliance and/or reporting purposes.

The emission tracking system 310 may be configured to validate the emission monitoring devices 375 to ensure that the received signals and data from devices 375 are accurate. The emission tracking system 310 can accomplish this by checking the emission monitoring devices 375 for certification. If the emission monitoring devices 375 are found to be certified by a regulatory body, no further validation may be required. On the other hand, if the emission tracking system 310 determines that the emission monitoring devices 375 are not certified, the emission tracking system 310 may validate the emission monitoring devices 375, for example, by carrying out a calibration check.

In one example, the emission tracking system 310 validates the data received from sensors 370 and/or emission monitoring devices 375 by transmitting a set of test signals to the sensors 370 and/or emission monitoring devices 375. The test signals are selected such that they are within the spectrum of the sensor 370 and/or emission monitoring device 375. For example, in one case, a set of test signals are selected such that one test signal it at a low end of sensor 370 and/or emission monitoring device 375 spectrum, another test signal is at a high end of sensor 370 and/or emission monitoring device 375 spectrum, and other test signals are within the spectrum. In another case, two test signals are selected and transmitted to the sensors 370 and/or emission monitoring devices 375, where the first test signal is at a low end of sensor 370 and/or emission monitoring device 375 spectrum and the second test signal is at a high end of sensor 370 and/or emission monitoring device 375 spectrum.

The test signals are selected such that the responses to the test signals are part of the operational parameters of the sensors 370 and/or emission monitoring devices 375, and can be predicted by the emission tracking system 310. The emission tracking system 310 then monitors the responses to the test signals from the sensors 370 and/or emission monitoring devices 375, and compares the responses to the predicted responses. In the event that the actual responses match the predicted responses, the emission tracking system 310 validates the sensors 370 and/or emission monitoring devices 375.

In another example, the emission tracking system 310 validates the data received from sensors 370 and/or emission monitoring devices 375 by measuring a known parameter of the sensors 370 and/or emission monitoring devices 375, and comparing the known value to the measured value to determine the accuracy of the sensors 370 and/or emission monitoring devices 375. For example, a thermistor can be validated by the emission tracking system 310 by measuring the resistance of the thermistor. The resistance of the thermistor is a principle operating parameter of the thermistor and is, therefore, a known value. The emission tracking system 310 compares the known resistance value of the thermistor with the measured resistance value, and determines if the thermistor is faulty or not based on the comparison.

In some cases, where the emission monitoring devices 375 are configured to monitor more than one greenhouse gas emissions generated, directly or indirectly, by the entity 305, the emission tracking system 310 may be configured to prompt the emission monitoring devices 375 to transmit raw emission data and/or total emission output measurement data for selected types of greenhouse gases only. In some other cases, the emission tracking system 310 is configured to extract or filter out data of interest, i.e. raw emission data and/or total emission output measurement data for selected types of greenhouse gases, from the stream of mixed data received for all types of monitored greenhouse gases.

As illustrated, monitoring system 355 also includes internal secondary sources 352. Internal secondary sources 352 can be defined as one or more units, devices and/or systems within the premises of the entity 305 that provide secondary data that can be used to estimate one or more greenhouse gas emissions associated with the entity 305. The internal secondary sources 352 do not directly monitor the amount of greenhouse gas emissions generated by the entity 305.

Examples of internal secondary sources 352 for an entity, such as a vehicle, may include one or more devices used to determine fuel levels, brake life, tire pressure etc. of the vehicle. Data from these sources can be used by the emission tracking system 310 to estimate greenhouse gas emissions from the vehicle.

In another example, the internal secondary sources 352 for a vehicle may include one or more devices configured to monitor the parameters of the engine of the vehicle. Such devices may include a transponder connected to the on-board diagnostics (OBD) port of the engine to capture engine data through the engine control module (ECM). The transponder may be connected to the OBD port using protocols such as J1939, ISO 15765-4 etc. Engine operation data from the ECM via the OBD port can be used by the emission tracking system 310 to estimate greenhouse gas emissions from the vehicle.

In cases where there is no ECM or the ECM does not provide the necessary data, the internal secondary sources 352 may include other sensors or devices connected to the vehicle or the engine of the vehicle that monitor engine operations. Data from these sensors or devices can be used by the emission tracking system 310 to estimate greenhouse gas emissions from the vehicle.

In another example, where entity 305 is a power generation facility, such as a power generation facility 105d of FIG. 1, the internal secondary sources 352 may include one or more devices configured to interact with and monitor the program logic control (PLC) of the power generation facility.

In another example, where entity 305 is a manufacturing or an industrial facility, such as an industrial facility 105b of FIG. 1, the internal secondary sources 352 may include one or more devices configured to monitor the methods and processes used in the facility.

Similarly, in another example, where entity 305 is a factory or an industrial facility, such as industrial facility 105b of FIG. 1, the secondary systems 360 may include one or more sensors configured to monitor emissions of fluorinated gases such as Hydrofluorocarbons (HFCs), Perfluorocarbons (PFCs), Sulfur hexafluoride (SF6) & Nitrogen trifluoride (NF3), etc.

While the entity 305 in the illustrated embodiment of FIG. 3 is shown to include primary sources 350, such as sensors 370 and emission monitoring devices 375, and internal secondary sources 352, it may be understood that not all entities 305 include all of these primary and secondary sources for monitoring greenhouse gas emissions. In some cases, the entity 305 may only include primary sources 350 or internal secondary sources 352, but not both. Similarly, in some cases, the entity 305 may only include sensors 370 or emission monitoring devices 375, but not both.

In some other examples, the entity 305 may not be equipped with any of the illustrated primary 350 and secondary 352 sources. In such cases, the emission tracking device 320 may be configured to interface with external secondary system 360 to estimate greenhouse gas emissions generated, directly or indirectly, by the entity 305.

The external secondary system 360 is analogous to internal secondary sources 352 but differs from the latter with respect to its location. Similar to the internal secondary sources 352, data received from the external secondary system 360 can be used to estimate greenhouse gas emissions for entity 305.

While the internal secondary sources 352 are described as sources present within the premises of the entity 305, the external secondary system 360 includes sensors, units, devices and/or systems not located within the premises of the entity 305. In some cases, external secondary system 360 may be located at a different entity. For example, if entity 305 is a power plant, electricity consumption data from households connected to the power plant can be used to estimate the carbon dioxide emissions from the power plant. In this example, the devices or systems that are used to monitor the electricity consumption at the households connected to the power plant constitute the external secondary system 360.

In some cases, the external secondary system 360 may include one or more servers or databases that receive and store emission related data from one or more of the primary sources 350 and internal secondary sources 352 of the entity 305. For example, in an entity 305, such as a household dwelling, the devices or systems configured to measure electrical consumption at the dwelling may be additionally configured to transmit the electrical consumption data to a cloud server. In this example, the cloud server containing the electrical consumption data of the households constitutes an external secondary system 360.

In the illustrated embodiment, platform 300 also includes a regulation system 340, which can be defined as any server or combination of servers operated and maintained by a regulation authority, or a third party receiving information from a regulation authority. A regulation authority may include any regional, provincial, federal and/or international (e.g. United Nations) body. Regulation system 340 is configured to provide regulatory information, such as standards, tax codes, statues, regulations, policies etc., corresponding to one or more greenhouse gasses.

Some non-limiting examples of information provided by the regulation system 340 includes acceptable and nonacceptable amounts of greenhouse gas emissions from an entity; techniques to reduce or minimize greenhouse gas emissions from various entities; fines or penalties associated with certain greenhouse gas emission levels; credits available for reducing greenhouse gas emission levels; tax ramifications of greenhouse gas credits; trade policies for trading greenhouse gas credits, etc.

The emission tracking system 310 interacts with the regulation system 340 via network 315 to receive appropriate regulation information for tracking (e.g. measuring, reporting, etc.) purposes. The regulation system 340 is constantly updated based on changes in existing regulations or introduction of new regulations.

As illustrated, platform 300 also includes an emission trading or trading system 330, which can be defined as a server or a combination of servers configured to facilitate trade of greenhouse gas emission credits between suppliers and buyers. Trading system 330 may include a website, an application, a central forum, an exchange or any other platform allowing individuals to enroll into the platform and carry out a trade. In some cases, the trading system 330 includes a platform where individuals can register and create respective accounts.

The trading system 330 interacts with the regulation system 340 via network 315. The regulation system 340 governs the trading system 330 and provides the framework for trading in greenhouse gas emission credits to the trading system 330. Similarly, emission tracking system 310 interacts with the trading system 330 via network 315 and provides the individuals on the trading system 330 with emission credits availability, emission reports, and other data that may be useful for trading on the platform.

In the illustrated embodiment, platform 300 comprises an emission tracking system 310, which may be a single device, or a collaboration of multiple devices. In the illustrated embodiment, the emission tracking system includes an emission tracking device 320 and an external processing device 325.

The emission tracking device 320 may be any networked computing device including a processor and memory. The emission tracking device 320 interacts with the other systems and devices on the platform 300 via network 315.

The emission tracking device 320 is configured to interact with the monitoring system 355 of the entity 305 and receive one or more of raw emission data (e.g. electrical signals from sensors 370, as discussed above), total emission output measurement (e.g. from emission measuring devices 375, as discussed above), secondary emission related data (e.g. from secondary internal sources 352), or a combination of these.

In some cases, the emission tracking device 320 is required by the regulation system 320 to monitor a particular type of greenhouse gas emission from an entity 305. In such cases, the emission tracking device 320 extracts the relevant emission related information corresponding to the particular type of greenhouse gas emission from all the data received from the monitoring system 355 of the entity 305. Optionally, the emission tracking device 320 can prompt the monitoring system 355 to only monitor the particular type of greenhouse gas emission and/or only transfer emission data related to the particular type of greenhouse gas emission.

In various cases, the monitoring system 355 of the entity 305 may be updated from time to time. This may be done to incorporate new and technologically advanced sensors 370, emission monitoring devices 375 and/or secondary sources within the premises of the entity 305. Such changes may be required by the regulation system 340. Alternatively, such changes may be part of periodic update and maintenance of the entity 305. In such cases, the emission tracking device 320 is configured to interface with any new or additional systems or devices introduced in the monitoring system 355 of the entity 305. This may be accomplished by updating the hardware, software and/or firmware of the emission tracking device 320.

As discussed above, the emission tracking device 320 can receive raw data from the monitoring system 355 and process this data to generate a total emission output measurement for one or more types of greenhouse gas emissions. For example, emission tracking device 320 may receive electrical signals monitored by one or more sensors 370 as part of raw emission data. In such cases, the emission tracking device processes the received data and calculates or generates a value corresponding to the received data. This value indicates the total emission output for a particular type of greenhouse gas generated, directly or indirectly, by the entity 305. In another example, emission tracking device 320 may receive secondary data from one or more internal secondary sources 352, and the emission tracking device 320 may then process the received secondary data to estimate the greenhouse gas emissions generated, directly or indirectly, by the entity 305.

In some cases, the emission tracking device 320 may receive the total emission output measurements from the monitoring system 355 itself, such as, from emission monitoring devices 375. In such cases, the emission tracking device 320 stores and compiles the received measurements for analysis by the external processing device 325.

As discussed above, the emission tracking device 320 is also configured to audit the monitoring system 355, including sensors 370, emission monitoring devices 375 and internal secondary sources 352. An advantage of auditing the monitoring system 355 is to ensure accurate and consistent monitoring and measurement of greenhouse gas emissions generated, directly or indirectly, by the entity 305.

In various cases, the emission tracking device 320 is configured to convert the emission data, including raw data, secondary data and measurement data into a format compatible with external processing device 325. The emission tracking device 320 is also configured to store and catalog emission data in any manner or format that may be prescribed by external processing device 325, regulation system 340, entity 305, or any other interested party.

The emission tracking device 320 is configured to transmit the emission data, in original or converted form, to the external processing device 325. In some cases, the emission tracking device 320 may encrypt the emission data prior to transmission.

The external processing device 325 may be any networked computing device including a processor and memory, such as a computer, workstation, server, or a combination of these. External processing device 325 is configured to interact with other systems or devices of platform 300 via network 315.

The external processing device 325 is configured to receive emission data, including raw data, measurements, secondary data and/or analyses etc. from emission tracking device 320. The external processing device 325 is further configured to analyze and process the received data and generate suitable emission reports.

For example, the external processing device 325 may be configured to analyze the received data to determine a greenhouse gas emission offset or credit for an entity 305 by comparing the total emission outputs from the entity 305 at two separate times, and determining the improvements in the greenhouse gas emissions from the entity 305 in that time period.

On the other hand, the external processing device 325 may also be configured to analyze the total emission output from the entity 305 at a given time, and recommend changes to the entity to reduce the generation of the greenhouse gas emissions from the entity 305.

In some cases, the external processing device 325 may be configured to analyze the received data and detect data tampering. This may be done by comparing the received data for an entity 305 to historical trends available for that entity 305. In addition to the received data, the external processing device 325 can also audit the monitoring system 355 based on the received data.

The external processing device 325 is also configured to generate reports based on the emission data and analysis. The reports may be generated for the regulation system 340, entity 305 or upon a request of another interested party. In some cases, the external processing device 325 may receive report templates that may be provided by a regulation system 340 or entity 305. In such cases, the external processing device 325 is configured to generate reports based on the templates.

The external processing device 325 may generate a variety of reports, including, reports for types of greenhouse gas emissions being monitored, the entity's emission baseline, amount of emissions generated, the monitoring period, total emission output for tax purposes, variation from the baseline, government or industry standard, variation from the standard, amount of carbon offset available for trading, amount of carbon offset required to balance the excess emissions, compliance status, validation information for the monitoring system 355, etc.

In some cases, the generated reports are used by entities 305 or individuals to trade on trading system 330. In some other cases, the generated reports are used by entities 305 or individuals for tax purposes etc.

The external processing device 325 is also configured to communicate with the emission tracking device 320 to instruct the device 320 regarding which greenhouse gas emissions to track within an entity 305. In addition, the external processing device 325 is also configured to communicate with the emission tracking device 320 to instruct the device 320 regarding what data to extract and transmit to the external processing device 325.

In some cases, the external processing device 325 allows entities 305 or individuals to register with the emission tracking system 310 by creating an account. The external processing device 325 may allow an individual to register two or more emission tracking devices 320 in their account. For example, if an individual wants to track greenhouse gas emissions from a number of entities 305 owned or controlled by the individual, the individual may choose to use one emission tracking device 320 per entity. In a scenario where an individual owns a vehicle, a house, and a factory, the individual may register three emission tracking devices 320 in their account, where each emission tracking device 320 is configured to uniquely monitor each of the vehicle, house and the factory. The individuals can also activate or deactivate various emission tracking devices 320 from their account.

In another example, where an individual owns or controls two or more entities 305, the individuals can use the same emission tracking device 320 for all the entities 305. In some cases, the purpose of the emission tracking device 320 can be redefined or changed from the account. This allows the emission tracking device 320 to stop monitoring one entity and start monitoring another entity owned by the individual.

Figure 5:
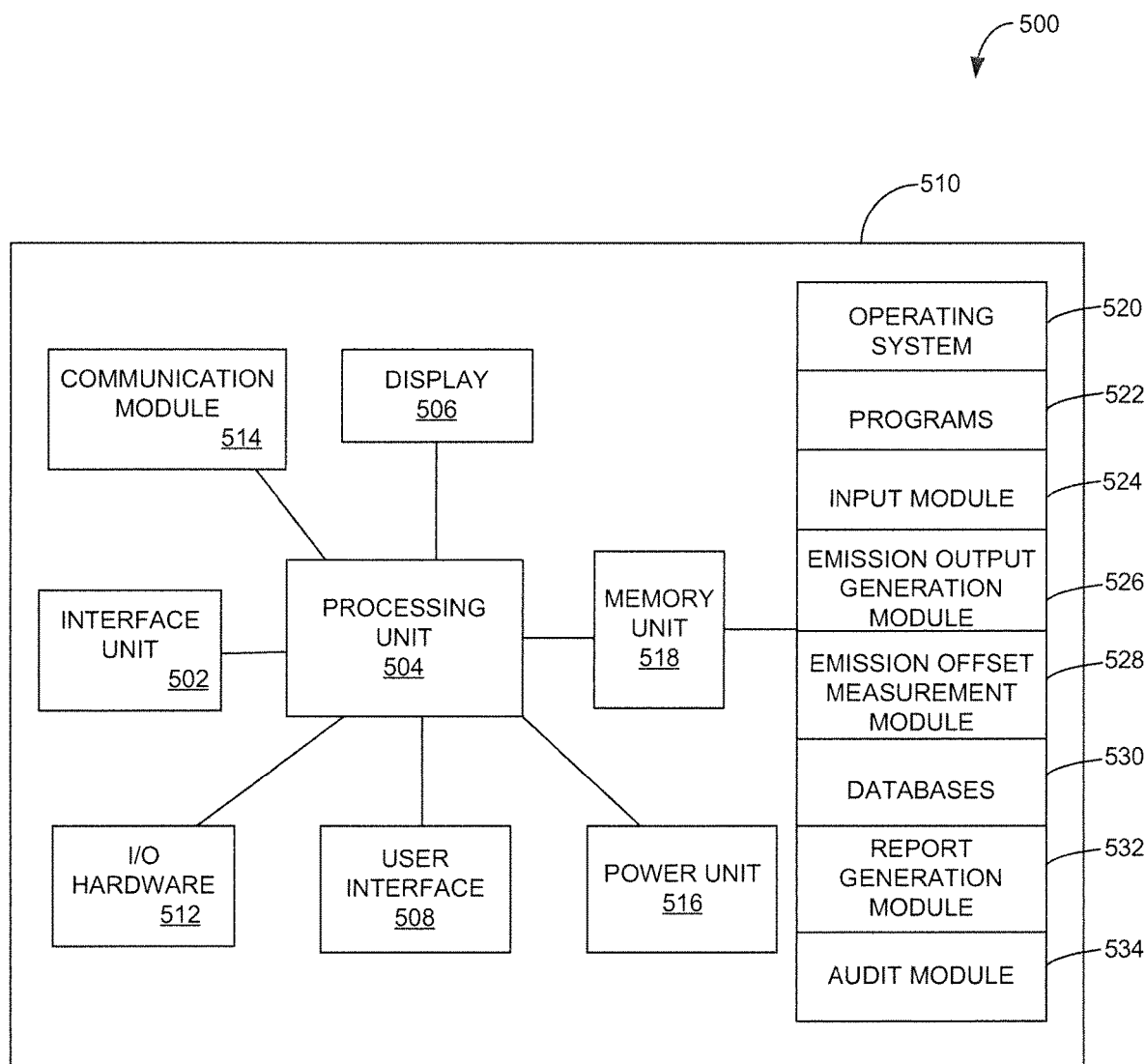
FIG. 5 is an example of a block diagram of an emission tracking system.

Reference is next made to FIG. 5, illustrating a block diagram 500 of an emission tracking system, such as emission tracking system 310 of FIG. 3, according to an example embodiment. The system 500 is provided as an example and there can be other embodiments of the system 500 with different components or a different configuration of the components described herein. The system 500 further includes several power supplies (not all shown) connected to various components of the system 500 as is commonly known to those skilled in the art. In general, a user, such as an operator, may interact with an emission tracking unit 510 of the system 500 to initiate tracking of one or more types of greenhouse gas emissions associated with an entity.

The emission tracking unit 510 comprises an interface unit 502, a processing unit 504, a display 506, a user interface 508, Input/Output (I/O) hardware 512, a communication module 514, a power unit 516 and a memory unit 518.

The memory unit 518 comprises software code for implementing an operating system 520, various programs 522, an input module 524, an emission output generation module 526, an emission offset measurement module 528, one or more databases 530, a report generation module 532 and an audit module 534.

The processing unit 504 controls the operation of the emission tracking unit 510. The processing unit 504 can be any suitable processor, controller or digital signal processor that can provide sufficient processing power depending on the configuration, purposes and requirements of the emission tracking unit 510 as is known by those skilled in the art. For example, the processing unit 504 may be a high performance general processor. In alternative embodiments, the processing unit 504 can include more than one processor with each processor being configured to perform different dedicated tasks. In alternative embodiments, it may be possible to use specialized hardware to provide some of the functions provided by the processing unit 504.

The display 506 can be any suitable display that provides visual information depending on the configuration of the emission tracking unit 510. For instance, the display 506 can be a cathode ray tube, a flat-screen monitor, an LCD display and the like if the emission tracking unit 510 is a desktop computer. In other cases, the display 506 can be a display suitable for a laptop, tablet or handheld device such as an LCD-based display and the like.

The user interface 508 can include at least one of a mouse, a keyboard, a touch screen, a thumbwheel, a track-pad, a track-ball, a card-reader, voice recognition software and the like again depending on the particular implementation of the emission tracking unit 510. In some cases, some of these components can be integrated with one another.

The interface unit 502 can be any interface that allows the emission tracking unit 510 to communicate with other devices or computers. In some cases, the interface unit 502 can include at least one of a serial port, a parallel port or a USB port that provides USB connectivity. The interface unit 502 can also include at least one of an Internet, Local Area Network (LAN), Ethernet, Firewire, modem or digital subscriber line connection. Various combinations of these elements can be incorporated within the interface unit 502.

The I/O hardware 512 is optional and can include, but is not limited to, at least one of a microphone, a speaker and a printer, for example.

The communication module 514 can include wired or wireless connection capabilities. The communication module 514 can include a radio that communicates utilizing CDMA, GSM, GPRS or Bluetooth protocol according to standards such as IEEE 802.11a, 802.11b, 802.11g, or 802.11n. The communication module 514 can be used by the emission tracking unit 510 to communicate with other devices or computers.

The power unit 516 can be any suitable power source that provides power to the emission tracking unit 510 such as a power adaptor or a rechargeable battery pack depending on the implementation of the emission tracking unit 510 as is known by those skilled in the art.

The memory unit 518 can include RAM, ROM, one or more hard drives, one or more flash drives or some other suitable data storage elements such as disk drives, etc. The memory unit 518 is used to store an operating system 520 and programs 522 as is commonly known by those skilled in the art. For instance, the operating system 520 provides various basic operational processes for the emission tracking unit 510. The programs 522 include various user programs so that a user can interact with the emission tracking unit 510 to perform various functions such as, but not limited to, viewing and manipulating data as well as sending messages as the case may be.

The memory unit 518 may also accept data from one of the input devices, the input module 524, the emission output generation module 526, the emission offset measurement module 528, the report generation module 532 and the audit module 534. The memory unit 518 uses the received data to define and store emission records.

Each emission record may identify a type of emission monitored at an entity, an identifier for the entity, the time of monitoring and the determined greenhouse gas emission output corresponding to the monitored greenhouse gas emission for the entity. The emission record may additionally include the source of emission monitoring (e.g. one or more sensors 370, emission monitoring devices 375, internal 352 and/or external 360 secondary sources), and the emission data received from the sources.

In one embodiment, the memory unit 518 receives customer information and creates customer records. In this embodiment, the emission tracking unit 510 allows customers to register and create accounts as discussed herein. Each customer record can include one or more types of information such as customer identifier (e.g. name, address, etc.), number and identification of entities owned or controlled by the customer, emission sources available to monitor greenhouse gas emissions associated with the entities, emission data received from the emission sources, emission output values corresponding to the emission data, emission offset measurements, emission reports, audit data, among other things.

The emission tracking unit 510 allows the customers to communicate with the unit 510 via input module 524. The customers can log in and view their accounts remotely. The customers can also define the purpose and functionality of the emission tracking unit 510 in terms of entities and types of greenhouse gas emissions to monitor. The customers can additionally define the categories to include in emission reports, and request the generation of one or more emission reports.

The input module 524 interacts with at least one of the memory unit 518 and the databases 530 for receiving emission data associated with one or more types of emissions from an entity. The input module 524 may interface with one or more emission sources, such as one or more sensors 370, emission monitoring devices 375, internal 352 and/or external 360 secondary sources etc., and receive emission data corresponding to greenhouse gas emissions associated with an entity. In some cases, the input module 524 may receive emission data via user interface 508 where a user may manually enter the emission data corresponding to greenhouse gas emissions from the entity. The input module 524 may also interface with one or more client devices, such as personal computers, phones etc., to receive customer registration information in order to create customer accounts.

The emission output generation module 526 interacts with at least one of the memory unit 518 and the databases 530 to process the emission data to determine an emission output value. The emission output generation module 526 may processes the emission data based on programs 522. In some cases, the emission data may be processed based on regulations prescribed by a regulation system, such as regulation system 340 of FIG. 3.

The emission output measurement module 528 interacts with at least one of the memory unit 518 and the databases 530 to process the emissions outputs generated from the emission output generation module 526 at various times, and generate a measurement of changes (e.g. improvements, deteriorations etc.) in the greenhouse gas emissions associated with an entity. The emission output generation module 528 generates an emission offset that can be traded using a trading system, such as trading system 330 of FIG. 3. In some cases, a tax grant, a credit, a fine, a penalty or some other consequence may result based on the emission offset measurement generated by module 528.

The databases 530 can be used to store data for the system 500 such as regulation standards, report templates, historical trends etc. The databases 530 can also store other information required for the operation of the programs 522 or the operating system 520 such as dynamically linked libraries and the like.

The report generation module 532 interacts with at least one of the memory unit 518 and the databases 530 to generate one or more reports based on the emission output values generated by module 526 and emission offset measurements generated by module 528. The report generate module 532 may base the emission reports on templates stored in databases 530.

The audit module 534 interacts with at least one of the memory unit 518 and the databases 530 to audit the various data and measurements, and the methods and processes of obtaining such data and measurements. The audit module 534 audits the various emission sources, such as sensors 370, emission monitoring devices 375, internal 352 and/or external 360 secondary sources etc. The audit module 534 also audits the emission data and calculated or estimated emission output values and offset measurement values. The audit module 534 also audits the reports for compliance.

The emission tracking unit 510 is additionally configured to carry out other functionalities of an emission tracking system, such as emission tracking system 310 of FIG. 3, as discussed in this document.

Reference is again made to FIG. 3 to illustrate an example application of the various embodiments disclosed herein in an agricultural sector. An agricultural entity may include one or more farms and other structures used in farming operations. Such structures may include buildings to house families and workers, as well as livestock, machinery (e.g. tractors, combines, harvesters etc.), and crops. Such structures may store seeds, hay, fodder, grains, fertilizers, pesticides, other chemical substances used in farming, etc. In some cases, the agricultural entity may contain other entities, such as on road and off road entities 105*h*, residential entity 105*a*, industrial entity 105*b* etc. of FIG. 1.

In an agricultural entity, there may be many sources of greenhouse gas emissions. For example, chemicals used in fertilizers, pesticides etc. may be a direct source of greenhouse gas emissions. Similarly, other substances containing one or more chemicals, such as ammonia sulfide, potassium nitrate, potash, hydrogen sulfide, charcoal, etc. may also contribute to greenhouse gas emissions.

Use and operation of farm machinery may also directly or indirectly contribute towards greenhouse gas emissions. As well, use of vehicles, such as on road and/or off road vehicles, in and around the farms and the buildings may also contribute towards the greenhouse gas emissions. In addition, the operation of the farming structures, including barns and buildings, may also directly or indirectly contribute towards the greenhouse gas emissions.

The emission tracking system 310 disclosed herein may be used to determine the amount of greenhouse gas emissions resulting from the various sources of emissions discussed above. For example, an emission monitoring system, such as system 355, may be used to determine the amount of greenhouse gas emissions using sensors 370, secondary sources 352, secondary system 360 etc.

In one example, the amount of greenhouse gas emissions resulting from the use of fertilizers, pesticides or other chemical substances may be determined by the emission tracking system 310 in conjunction with the regulation system 340. In this case, the regulation system 340 may be configured to provide a correlation between the chemicals used in the fertilizers, pesticides etc. and the greenhouse gas emissions resulting from them. Such correlation information may be made available by a government body or a third party based on research or experiment. In a non-limiting example, the regulation system 340 may be configured to provide that the greenhouse gas emissions resulting from every 100 kilograms of a particular kind of fertilizer is approximately 2 grams of nitrous oxide.

In some cases, the regulation system 340 may provide more specific emission related information by taking into account factors such as the type of fertilizer, the concentration of fertilizer, the storage facility for the fertilizer (e.g. open storage, close storage etc.), any other such factors. The regulation system 340 may be similarly configured to provide a correlation between pesticides and/or other chemicals, and greenhouse gas emissions.

Once the correlation information between the fertilizers, pesticides etc. and greenhouse gas emissions is received from the regulation system 340, the emission tracking system 310 may use this information to determine the amount of greenhouse gas produced by the agricultural entity due to the use of such chemicals. The emission tracking system 310 may be configured to do so by applying the information received from the regulation system 340 to the specifics of the agricultural entity, such as the size of the farm as well as volume, amount and weight of the fertilizers, pesticides etc. use on the farm.

In some cases, the emission tracking system 310 may be configured to determine the amount of greenhouse gas emissions from the agricultural entity based on the toxicity characteristics of the sewage wastewater produced by the agricultural entity. Toxicity characteristics may be determined using internal secondary sources 352 and/or external secondary system 360 of FIG. 3. In some cases, the toxicity characteristics may be determined based on a third party analysis and may be directly provided into an emission tracking unit, such as the emission tracking unit 510 of FIG. 5.

In one example, the profile record of a farmer in an emission tracking unit includes entities such as one or more farms, livestock, one or more vehicles and one or more buildings such as a barn. In such cases, there may be many sources of greenhouse gas emissions. For example, cow or cattle burping or belching, livestock waste management and/or biomass burning may result in production of methane. Use of fertilizers and pesticides may result in production of nitrous oxide. Farming systems employed on the farm may also result in emission of greenhouse gases. In addition, burning of carbon based fuels in the vehicles or farm equipments and use of electricity in the buildings may also contribute towards the greenhouse gas emissions. In such cases, the total greenhouse gas emissions associated with this farmer or the corresponding profile record is determined based on the greenhouse gas emissions resulting from each one of these entities.

Figure 4:
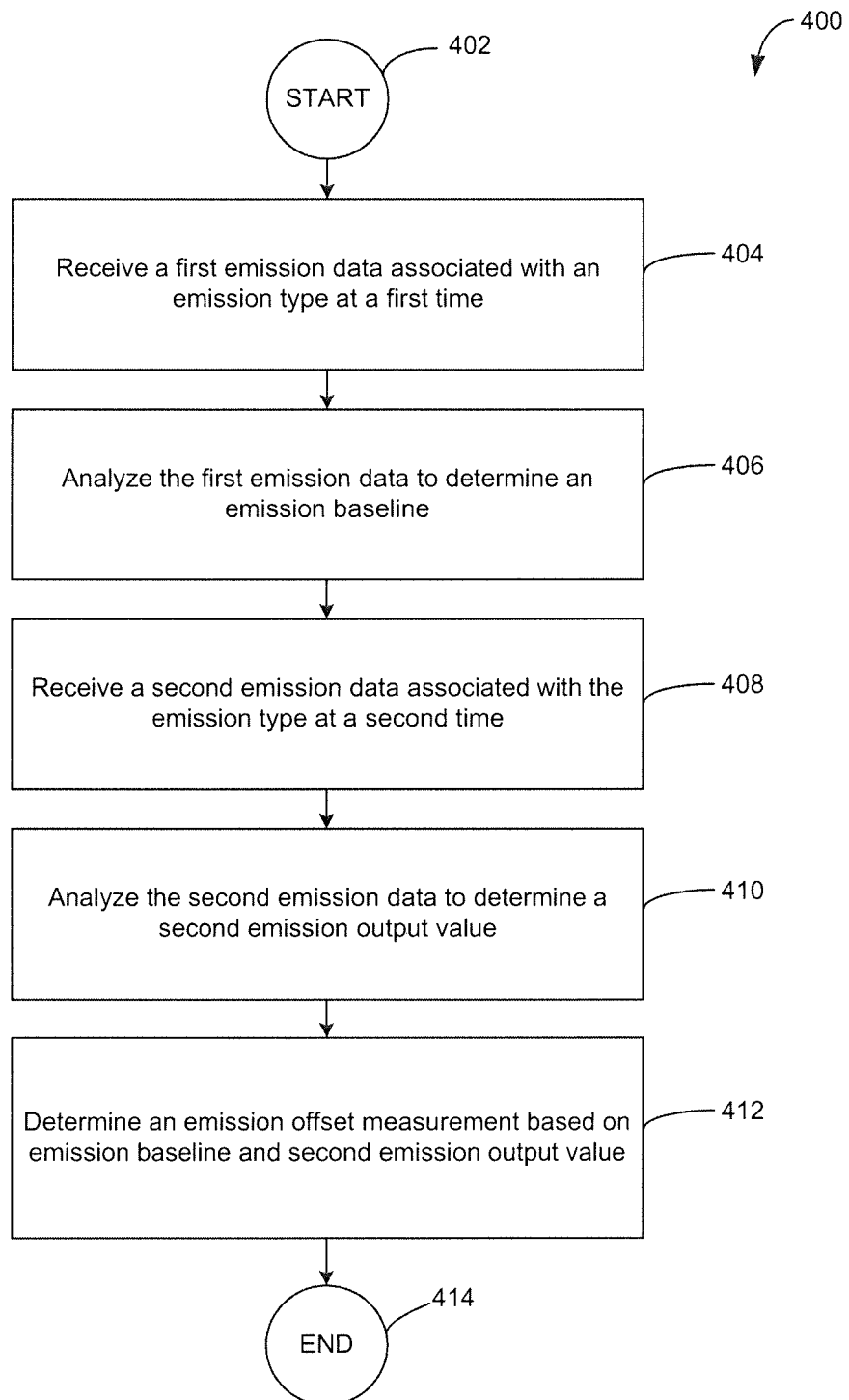
FIG. 4 is an example of a process of tracking greenhouse gas emissions associated with an entity.

Reference is next made to FIG. 4, illustrating a process 400 carried out by an emission tracking system, such as the emission tracking system 310 of FIG. 3, according to the teachings herein.

The process begins at step 402. At step 404, the emission tracking system 310 receives a first emission data at a first time. The first emission data corresponds to one or more different types of greenhouse gas emissions generated, directly or indirectly, by an entity, such as entity 305 of FIG. 3. The first emission data may be received from a monitoring system, such as monitoring system 310 of FIG. 3.

In some cases, the first emission data is received from the primary sources, such as sensors, emission measuring devices etc., within the entity 305. In some other cases, the first emission data is received from the internal secondary sources within the entity 305. In some further cases, the first emission data may be received from external secondary sources, such as external secondary system 360 of FIG. 3. The first emission data may also be received from a combination of these sources.

The first emission data includes any data that can be used to determine the amount of greenhouse gas emissions generated from an entity. The first emission data can include direct data from devices, such as sensors, CEMs, PEMs etc., monitoring greenhouse gas emissions directly. The first emission data can also include data from secondary sources, where the data can be analyzed to estimate the amount of greenhouse gas emissions generated from an entity. The secondary sources can be located within the premises of the entity, or remotely from the entity.

At step 406, the emission tracking system 310 analyzes the first emission data received at the first time to determine a first emission output value. The first emission output value indicates the amount of emissions of a particular greenhouse gas generated, directly or indirectly, by the entity.

This emission output value from emission data received at the first time forms an emission baseline. The baseline can be used in several methods for comparison. For example, the baseline can be compared to the industry standard to determine the carbon-offset. The baseline can be used to determine if a new technology or application reduces emissions by comparing before and after emission output values.

In cases where emission data is received from secondary sources, hysteresis or statistical analysis can be done to determine the first emission output value. In cases where emission data is received from primary sources, suitable processes or calculations can be used to convert the received emission data into emission output value.

At step 408, the emission tracking system 310 receives a second emission data at a second time corresponding to the same greenhouse gas or gases for which first emission data was received at step 404. The second emission data is received in any of the ways discussed above in relation to the first emission data.

The second emission data is received after implementing a certain change within the monitored entity 305 or within another entity that affects the greenhouse gas generation at the monitored entity 305. For example, the monitored entity 305 may be equipped with a $CO_2$ scrubber to remove or reduce the amount of $CO_2$ generated by the entity 305. In another example, the monitored entity 305 as well as other entities affecting the greenhouse gas generation at the monitored entity 305 may undergo maintenance and repair to remove inefficient/old equipment. Such emission reduction changes may be recommended by the emission tracking system 310, a regulation system 340 or any other third party system.

At step 410, the emission tracking system 310 analyzes the second emission data received at the second time to determine a second emission output value. The emission data may be converted into an emission output value based on the various teachings herein.

At step 412, the emission tracking system 310 determines an emission offset measurement based on the first and the second emission output values. The emission offset measurement indicates the change in the total emissions generated, directly or indirectly, by the entity between the first time and the second time.

The emission offset measurement is an emission credit in the event that the greenhouse gas emissions generated by the entity 305 have reduced from the first time to the second time. On the other hand, the emission offset measurement is an emission excess in the event that the greenhouse gas emissions generated by the entity 305 have increased from the first time to the second time.

Emission offset measurement can be used for trading, receiving grants and/or other ways of monetization based on regulations and standards governing the greenhouse gas emission framework in a region, province or country. Similarly, in the event of a negative emission offset measurement, fines and penalties can be imposed based on the emission framework in place. The process end at step 414.

Figure 6:
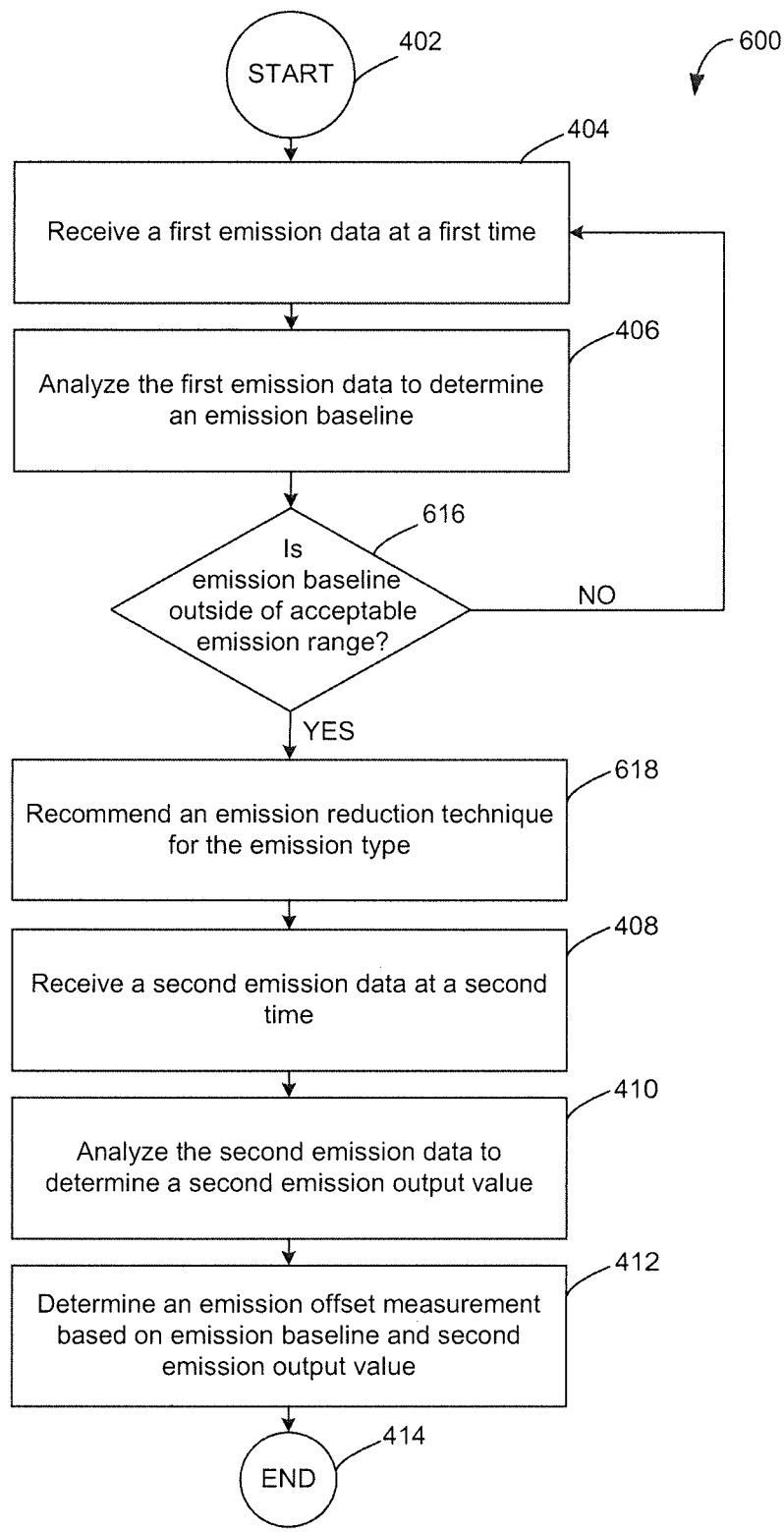
FIG. 6 is an example of a process of tracking greenhouse gas emissions associated with an entity.

Reference is next made to FIG. 6, illustrating a process 600 carried out by an emission tracking system, such as the emission tracking system 310 of FIG. 3, according to the teachings herein. Process 600 is analogous to process 400 of FIG. 4, and differs only in steps 616 and 618.

At step 616, the emission tracking system 310 determines if the first emission output value generated based on first emission data received at first time is within established regulations. The established regulations may be made available by a regulation system, such as regulation system 340 of FIG. 3. The established regulations may be received and stored in the emission tracking system 310, and may be constantly updated based on the changes to the regulations.

If it is established that the first emission output value is not within the established regulations, the process proceeds to step 618. Otherwise, the process proceeds to step 404.

At step 618, the emission tracking system 310 recommends one or more emission reduction techniques that can be implemented within the entity being monitored or other entities that affect the greenhouse gas generated, directly or indirectly, by the monitored entity.

In some cases, the emission tracking system 310 receives a list of one or more emission reduction techniques from the regulation system 340. The regulation system 340 may include a database of emission reduction techniques that may be updated periodically based on research and development in the field. The regulation system 340 may be maintained and updated by municipal, provincial, national and/or international government bodies.

In some cases, the emission tracking system 310 may transmit the emission output values, such as the first emission output value, to the regulation system 340, and the regulation system 340 may recommend appropriate emission reduction techniques based on factors such as type of entity, greenhouse gas emissions being monitored, generated emission output values, and amount of offset needed to balance the emission outputs etc.

In some other cases, the emission tracking system 310 may receive many emission reduction technique recommendations from the regulation system 340, and the emission tracking system 310 may shortlist the suitable emission reduction techniques based on factors such as type of entity, greenhouse gas emissions being monitored, generated emission output values, and amount of offset needed to balance the emission outputs etc.

In yet some other cases, the emission tracking system 310 may itself be equipped with emission reduction techniques, and may recommend one or more suitable techniques based on factors such as type of entity, greenhouse gas emissions being monitored, generated emission output values, and amount of offset needed to balance the emission outputs etc. The process then proceeds to steps 408-412 as discussed above.

In some cases, the emission offset measurement generated at step 412 may be used by the emission tracking system 310 to provide validation for emission reduction techniques recommended at step 618. For example, the emission tracking system 310 may be configured to monitor and log the types of emission reduction techniques recommended at step 618 and the emission offset measurement determined at step 412.

Since not all emission reduction techniques recommended at step 618 may be implemented by the monitored entity or other entities affecting the monitored entity, process 600 may have an optional step of receiving information regarding emission reduction techniques that have actually been implemented by the monitored entity or other entities affecting the monitored entity. In such cases, the emission tracking system 310 is configured to map the emission offset measurements to the implemented emission reduction techniques.

In some cases, the implemented techniques may be recorded in a database or a server of an external secondary system, such as external secondary system 340, and may be received by the emission tracking system 310 from the external secondary system 340.

One example of emission reduction technique that may be recommended by the emission tracking system 310 is a carbon sink. A carbon sink is a way of removing carbon (or other gasses) physically by changing the molecular structure of the gas. This can be done through natural or artificial methods. For example, a natural way to remove $CO_2$ is through photosynthesis, and can be accomplished by planting more trees and plants etc. An artificial method to remove or reduce $CO_2$ is by implementing a carbon scrubber device.

The emission tracking system 310 may, alternatively or additionally, also recommend maintenance programs to reduce carbon emissions. For example, emission tracking system 310 may recommend periodic greasing of the parts in motion on an entity, such as a vehicle or a machine, etc. This technique may increase the efficiency of the entity, and over time, reduce energy consumption by the entity. This reduction of energy may correspond to a reduction of greenhouse gas emission by the entity.

In some cases, the external secondary system 360 may be equipped with a maintenance program database used to record the various maintenance programs implemented for improving the greenhouse gas emissions associated with the entity 305. Such data may be recorded every time a new maintenance program (e.g. scheduled maintenance, greasing of moving parts, etc.) is implemented. In such cases, the emission tracking system 310 interfaces with the external secondary system 360 and determines the emission reduction techniques actually implemented. This data then becomes part of emission data used to determine emission output value for the entity.

Figure 7:
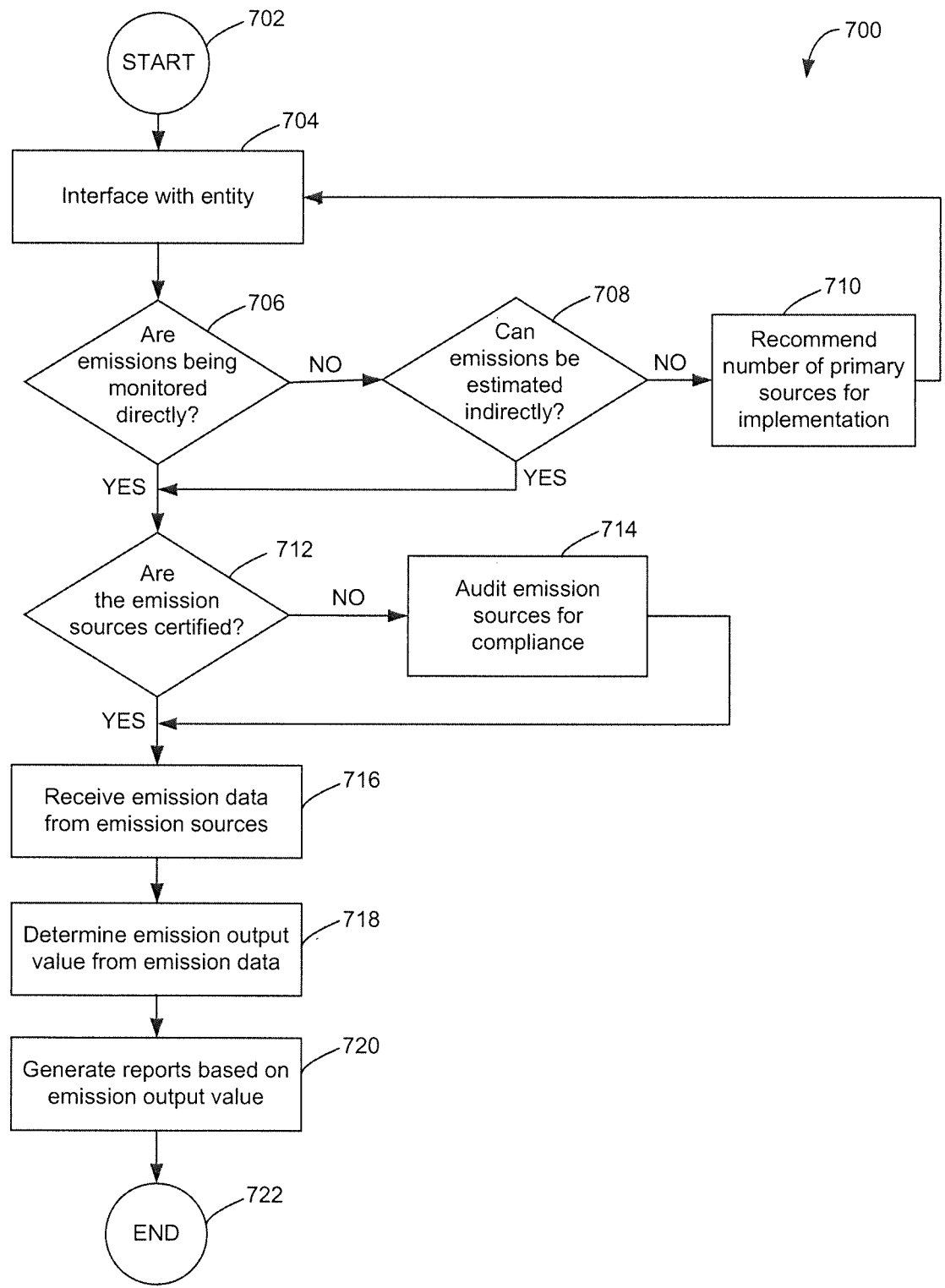
FIG. 7 is another example of a process of tracking greenhouse gas emissions associated with an entity.

Reference is next made to FIG. 7, illustrating a process 700 carried out by an emission tracking system, such as the emission tracking system 310 of FIG. 3, according to the teachings herein.

The process begins at step 702. At step 704, the emission tracking system 310 interfaces with an entity, such as entity 305, to monitor the amount of greenhouse gas emissions generated, directly or indirectly, by the entity 305. The emission tracking system 310 may become active and ready for tracking greenhouse gas emissions by an entity 305 based on a predetermined schedule. Alternatively, the emission tracking system 310 may become active and ready for tracking greenhouse gas emissions by an entity 305 based on an operator intervention.

At step 706, the emission tracking system 310 determines if entity 305 is being directly monitored for greenhouse gas emissions by primary sources, such as primary sources 350 of FIG. 3. The emission tracking system 310 may determine whether or not the entity 305 is equipped with one or more sensors 370 and/or emission monitoring devices 375 (such as CEM, PEM etc.) in order to determine the presence of primary sources 350.

If it is determined that the entity 305 is not being monitored by primary sources, the process proceeds to step 708. Otherwise, the process proceeds to step 712.

At step 708, the emission tracking system 310 determines if the greenhouse gas emissions generated, directly or indirectly, by the entity 305 can be monitored by secondary sources.

In this step, the emission tracking system 310 can determine if internal or external secondary sources, such as internal secondary sources 352 and external secondary system 360 of FIG. 3, are available to provide emission data that can be used to determine (e.g. estimate) the amount of greenhouse gas emissions generated, directly or indirectly, by the entity 305.

If it is determined that the entity 305 cannot be tracked for greenhouse gas emissions using secondary sources, then the process proceeds to step 710. Otherwise, the process proceeds to step 712.

At step 710, the emission tracking system 310 is configured to determine how many primary sources, such as sensors, CEM, PEM etc. are required to monitor the greenhouse gas emissions associated with the entity 305. The emission tracking system 310 can make this determination based on one or more factors such as type of entity 305, size or mass of entity 305, age of entity 305, historical emission trends of entity 305, number of greenhouse gas emissions generated by the entity 305, extent of variations in greenhouse gas emissions throughout the day, extent of variations in the concentration of the greenhouse gas emissions, number of sources of greenhouse gas emissions within the entity 305 etc.

In some cases, the emission tracking system 310 is also configured to determine how many primary sources, such as sensors, CEM, PEM etc. are required to monitor one or more other entities that affect the greenhouse gas emissions associated with the monitored entity 305. From step 710, the method proceeds to step 704.

Next, at step 712, the emission tracking system 310 determines if the monitoring system, consisting of primary and secondary sources of monitoring greenhouse gas emissions associated with the entity 305, is certified. This check may be advantageous to ensure correct and consistent monitoring and measurement of the greenhouse gas emissions associated with the entity 305. At this step, the emission tracking system 310 determines if all of the sources of emission data within the monitoring system are certified.

If it is determined that the monitoring system is not certified, the process proceeds to step 714. Otherwise the process proceeds to step 716. At step 714, the emission tracking system 310 audits the non-certified sources of emission data for compliance with regulation standards. The emission tracking system 310 may receive the standards related information from a regulation system, such as regulation system 340 of FIG. 3.

The emission tracking system 310 may use various tests or checks to determine if the sources of emission data comply with the standards. For example, the emission tracking system 310 can carry out a calibration check as discussed herein to audit the monitoring system. The emission tracking system 310 may alternatively or additionally rely on third party standard measuring companies or systems to provide the necessary checks. The process next proceeds from step 714 to 716.

Steps 716 and 718 of process 700 are analogous to steps 404 and 406 of FIGS. 4 and 6. At step 716, the emission tracking system 310 receives emission data corresponding to one or more greenhouse gas emissions associated with the entity 305. At 718, the emission tracking system 310 determines an emission output value based on the received emission data.

Next, at step 720, the emission tracking system 310 is configured to generate suitable reports based on the generated emission output values for one or more greenhouse gas emissions associated with the entity 305. For example, the emission tracking system 310 may generate one or more reports illustrating types of greenhouse gas emissions being monitored, the entity's emission baseline, amount of emissions generated, the monitoring period, total emission output for tax purposes, government or industry standard, variation from the standard, amount of carbon offset required to balance the excess emissions, etc. The process ends at step 722.

In some cases, the process 700 may proceed with steps 404-412 of FIG. 4 after step 712 of FIG. 7. In some other cases, the process 700 may proceed with steps 404-412, including steps 616 and 618, of FIG. 6 after step 712 of FIG. 7.

Numerous specific details are set forth herein in order to provide a thorough understanding of the exemplary embodiments described herein. However, it will be understood by those of ordinary skill in the art that these embodiments may be practiced without these specific details. In other instances, well-known methods, procedures and components have not been described in detail so as not to obscure the description of the embodiments. Furthermore, this description is not to be considered as limiting the scope of these embodiments in any way, but rather as merely describing the implementation of these various embodiments.

The invention claimed is:

1. A method for tracking at least one emission type generated by a vehicle, the method performed by one or more devices located within the vehicle, the vehicle generating one or more emissions types including the at least one emission type, the method comprising:
   determining if the vehicle is being monitored by one or more primary sources located within the vehicle for the at least one emission type, the one or more primary sources providing a direct measure of the at least one emission type;
   if the vehicle is being monitored by the one or more primary sources:
      receiving a first primary emission data associated with the at least one emission type at a first time;
      analyzing the first primary emission data received at the first time to determine a first emission output value designated as an emission baseline;
      receiving a second primary emission data associated with the at least one emission type at a second time, wherein the second primary emission data is received after implementation of at least one emission reduction step;
      analyzing the second primary emission data received at the second time to determine a second emission output value; and
   if the vehicle is not being monitored by the one or more primary sources;
      determining if the vehicle is being monitored by one or more secondary sources located within the vehicle for the at least one emission type, the one or more secondary sources providing an indirect measure of the at least one emission type;
      if the vehicle is being monitored by the one or more secondary sources;
         receiving a first secondary emission data associated with the at least one emission type at the first time;
         analyzing the first secondary emission data received at the first time to determine the first emission output value designated as the emission baseline;
         receiving a second secondary emission data associated with the at least one emission type at the second time wherein the second secondary emission data is received after implementation of at least one emission reduction step;
         analyzing the second secondary emission data received at the second time to determine the second emission output value; and
   determining an emission offset measurement corresponding to the at least one emission type based on the emission baseline and the second emission output value.

2. The method of claim 1, wherein the one or more primary sources comprise one or more emission sensors located within the vehicle, and wherein when the vehicle is being monitored by the one or more primary sources, the method further comprises interfacing with the one or more emission sensors to receive the first primary emission data and the second primary emission data, the one or more emission sensors being configured to measure the at least one emission type.

3. The method of claim 1, wherein the one or more primary sources comprise one or more emission monitoring devices located within the vehicle, and wherein when the vehicle is being monitored by the one or more primary sources, the method further comprises interfacing with the one or more emission monitoring devices to receive the first primary emission data and the second primary emission data, the one or more emission monitoring devices being configured to measure the at least one emission type.

4. The method of claim 1, wherein the one or more secondary sources comprise one or more secondary emission sources, and wherein when the vehicle is being monitored by the one or more secondary sources, the method further comprises interfacing with the one or more secondary emission sources to receive the first secondary emission data corresponding to the at least one emission type at the first time and the second secondary emission data corresponding to the at least one emission type at the second time.

5. The method of claim 1, further comprising comparing the emission baseline to an emission standard for the at least one emission type, and determining the at least one emission reduction step based on the comparison.

6. The method of claim 1, further comprising generating at least one emission report associated with the emission offset measurement.

7. The method of claim 1, further comprising determining carbon credits available for trading based on the emission offset measurement.

8. The method of claim 1, wherein the at least one emission type is selected from the group consisting of carbon monoxide, carbon dioxide, methane, ozone, chlorofluorocarbons, sulfur oxides, nitrogen oxides, non-methane volatile organic compounds, ammonia, and peroxyacetyl nitrate.

9. The method of claim 1, wherein the secondary sources comprise a transponder, connected to an on-board diagnostics (OBD) port associated with an engine control module (ECM) of the vehicle, and used for capturing engine operation data.

10. The method of claim 1, wherein the secondary sources comprise sensors connected to the vehicle, or the engine of the vehicle, for monitoring one or more of: engine operation parameters, fuel level and tire pressure.

11. A device for tracking at least one emission type generated by a vehicle, the device being located within the vehicle, the vehicle generating one or more emissions types including the at least one emission type, the device comprising at least one processor, the at least one processor being configured to:
   determine if the vehicle is being monitored by one or more primary sources located within the vehicle for the at least one emission type, the one or more primary sources providing a direct measure of the at least one emission type;
   if the vehicle is being monitored by the one or more primary sources:
      receive a first primary emission data associated with the at least one emission type at a first time;
      analyze the first primary emission data received at the first time to determine a first emission output value designated as an emission baseline;
      receive a second primary emission data associated with the at least one emission type at a second time, wherein the second primary emission data is received after implementation of at least one emission reduction step;
      analyze the second primary emission data received at the second time to determine a second emission output value; and if the vehicle is not being monitored by the one or more primary sources:
  determine if the vehicle is being monitored by one or more secondary sources located within the vehicle for the at least one emission type, the one or more secondary sources providing an indirect measure of the at least one emission type;
  if the vehicle is being monitored by the one or more secondary sources:
    receive a first secondary emission data associated with the at least one emission type at the first time;
    analyze the first secondary emission data received at the first time to determine the first emission output value designated as the emission baseline;
    receive a second secondary emission data associated with the at least one emission type at the second time, wherein the second secondary emission data is received ater implementation of at least one emission reduction step;
    analyze the second secondary emission data received at the second time to determine the second emission output value, and
  determine an emission offset measurement corresponding to the at least one emission type based on the emission baseline and the second emission output value.

12. The device of claim 11, wherein the one or more primary sources comprise one or more emission sensors located within the vehicle and wherein when the vehicle is being monitored by the one or more primary sources, the at least one processor is further configured to interface with the one or more emission sensors to receive the first primary emission data and the second primary emission data, the one or more emission sensors being configured to measure the at least one emission type.

13. The device of claim 11, wherein the one or more primary sources comprise one or more emission monitoring devices located within the vehicle, and the at least one processor is further configured to interface with the one or more emission monitoring devices to receive the first primary emission data and the second primary emission data, the one or more emission monitoring devices being configured to measure the at least one emission type.

14. The device of claim 11, wherein the one or more secondary sources comprise one or more secondary emission sources, and wherein when the vehicle is being monitored by the one or more secondary sources, the at least one processor is further configured to interface with the one or more secondary emission sources to receive the first secondary emission data corresponding to the at least one emission type at the first time and the second secondary emission data corresponding to the at least one emission type at the second time.

15. The device of claim 11, wherein the at least one processor is further configured to:
  compare the emission baseline to an emission standard for the at least one emission type; and
  determine the at least one emission reduction step based on the comparison.

16. The device of claim 11, wherein the at least one processor is further configured to generate at least one emission report associated with the emission offset measurement.

17. The device of claim 11, wherein the at least one processor is further configured to determine carbon credits available for trading based on the emission offset measurement.

18. The device of claim 11, wherein the at least one emission type is selected from the group consisting of carbon monoxide, carbon dioxide, methane, ozone, chlorofluorocarbons, sulfur oxides, nitrogen oxides, non-methane volatile organic compounds, ammonia, and peroxyacetyl nitrate.

19. The device of claim 11, wherein the secondary sources comprise a transponder, connected to an on-board diagnostics (OBD) port associated with an engine control module (ECM) of the vehicle, and used for capturing engine operation data.

20. The device of claim 11, wherein the secondary sources comprise sensors connected to the vehicle, or the engine of the vehicle, for monitoring one or more of: engine operation parameters, fuel level and tire pressure.

21. A computer-readable medium storing computer-executable instructions, the instructions for causing at least one processor, of a device located within a vehicle, to perform a method of tracking at least one emission type generated by the vehicle, the vehicle generating one or more emissions types including the at least one emission type, the method comprising:
  determining if the vehicle is being monitored by one or more primary sources located within the vehicle for the at least one emission type, the one or more primary sources providing a direct measure of the at least one emission type;
  if the vehicle is being monitored by the one or more primary sources:
    receiving a first primary emission data associated with the at least one emission type at a first time;
    analyzing the first primary emission data received at the first time to determine a first emission output value designated as an emission baseline;
    receiving a second primary emission data associated with the at least one emission type at a second time, wherein the second primary emission data is received after implementation of at least one emission reduction step;
    analyzing the second primary emission data received at the second time to determine a second emission output value;
  if the vehicle is not being monitored by the one or more primary sources:
    determining if the at least one emission type is being monitored by one or more secondary sources located within the vehicle, the one or more secondary sources providing an indirect measure of the at least one emission type;
    if the vehicle is being monitored by the one or more secondary sources;
      receiving a first secondary emission data associated with the at least one emission type at the first time;
      analyzing the first secondary emission data received at the first time to determine the first emission output value designated as the emission baseline:
      receiving a second secondary emission data associated with the at least one emission type at the second time, wherein the second secondary emission data is received after implementation of at least one emission reduction step;
      analyzing the second secondary emission data received at the second time to determine the second emission output value; and determining an emission offset measurement corresponding to the at least one emission type based on the emission baseline and the second emission output value.

22. The computer readable medium of claim 21, wherein the one or more primary sources comprise one or more emission sensors located within the vehicle, and wherein when the vehicle is being monitored by the one or more primary sources, the method further comprises interfacing with the one or more emission sensors to receive the first primary emission data and the second primary emission data, the one or more emission sensors being configured to measure the at least one emission type.

23. The computer readable medium of claim 21, wherein the one or more primary sources comprise one or more emission monitoring devices located within the vehicle, and wherein when the vehicle is being monitored by the one or more primary sources, the method further comprises interfacing with the one or more emission monitoring devices located within the vehicle to receive the first primary emission data and the second primary emission data, the one or more emission monitoring devices being configured to measure the at least one emission type.

24. The computer readable medium of claim 21, wherein the one or more secondary sources comprise one or more secondary emission sources, and wherein when the vehicle is being monitored by the one or more secondary sources, the method further comprises interfacing with the one or more secondary emission sources to receive the first secondary emission data corresponding to the at least one emission type at the first time and the second secondary emission data corresponding to the at least one emission type at the second time.

25. The computer readable medium of claim 21, wherein the method further comprises comparing the emission baseline to an emission standard for the at least one emission type, and determining the at least one emission reduction step based on the comparison.

26. The computer readable medium of claim 21, wherein the method further comprises generating at least one emission report associated with the emission offset measurement.

27. The computer readable medium of claim 21, wherein the method further comprises determining carbon credits available for trading based on the emission offset measurement.

28. The computer readable medium of claim 21, wherein the at least one emission type is selected from the group consisting of carbon monoxide, carbon dioxide, methane, ozone, chlorofluorocarbons, sulfur oxides, nitrogen oxides, non-methane volatile organic compounds, ammonia, and peroxyacetyl nitrate.

29. The computer readable medium of claim 21, wherein the secondary sources comprise a transponder, connected to an on-board diagnostics (OBD) port associated with an engine control module (ECM) of the vehicle, and used for capturing engine operation data.

30. The computer readable medium of claim 21, wherein the secondary sources comprise sensors connected to the vehicle, or the engine of the vehicle, for monitoring one or more of: engine operation parameters, fuel level and tire pressure.

* * * * *

UNITED STATES PATENT AND TRADEMARK OFFICE
CERTIFICATE OF CORRECTION

PATENT NO.         : 11,416,872 B2
APPLICATION NO.    : 16/875843
DATED              : August 16, 2022
INVENTOR(S)        : David Bridge and Ruston Jeroen Hoffman It is certified that error appears in the above-identified patent and that said Letters Patent is hereby corrected as shown below:

In the Claims

Claim 1, Column 27, Line 32, "sources;" should read -- sources: --.

Claim 1, Column 27, Line 39, "sources;" should read -- sources: --.

Claim 1, Column 27, Line 47, "second time wherein the second secondary...." should read -- second time, wherein the second secondary.... --.

Claim 12, Column 29, Line 29, "located within the vehicle and wherein...." should read -- located within the vehicle, and wherein.... --.

Claim 21, Column 30, Line 54, "sources;" should read -- sources: --.

Claim 21, Column 30, Line 59, "output value designated as the emission baseline:" should read -- output value designated as the emission baseline; --.

Signed and Sealed this
Twentieth Day of December, 2022

Katherine Kelly Vidal
*Director of the United States Patent and Trademark Office*